United States Patent
Sanicola-Nadel et al.

(10) Patent No.: US 6,664,385 B1
(45) Date of Patent: Dec. 16, 2003

(54) KIDNEY INJURY-RELATED MOLECULES

(75) Inventors: Michele Sanicola-Nadel, Winchester, MA (US); Joseph V. Bonventre, Wayland, MA (US); Catherine Hession, Hingham, MA (US); Takaharu Ichimura, South Burlington, VT (US); Henry Wei, Ossining, NY (US); Richard L. Cate, Weston, MA (US)

(73) Assignee: Biogen, Inc., Cambridge, MA (US)

( * ) Notice: Subject to any disclaimer, the term of this patent is extended or adjusted under 35 U.S.C. 154(b) by 0 days.

(21) Appl. No.: 09/197,970

(22) Filed: Nov. 23, 1998

Related U.S. Application Data

(63) Continuation-in-part of application No. PCT/US97/09393, filed on May 23, 1997.
(60) Provisional application No. 60/023,442, filed on Aug. 23, 1996, and provisional application No. 60/018,228, filed on May 24, 1996.

(51) Int. Cl.[7] .............................................. C07H 21/04
(52) U.S. Cl. .................... 536/23.4; 536/23.5; 435/69.1; 435/69.7; 435/325
(58) Field of Search ............................... 534/23.5, 23.4; 435/69.1, 69.7, 325

(56) References Cited

U.S. PATENT DOCUMENTS 5,622,861 A * 4/1997 Kaplan et al. ............ 435/253.3

FOREIGN PATENT DOCUMENTS

WO    WO 96/04376    2/1996

OTHER PUBLICATIONS

Feigelstock et al. J. Virology 72: 6621–6628, 1998.*
Skolnick et al. Tibtech vol. 18, Jan. 2000, pp. 34–38.*
The Protein Folding Problem and Testiary Ngo, Structure Prediction, Birkhauser Boston 1994.*
Ricger et al. Glossary of Genetics. 5th Edition Springer–Verlag, N.Y. pp. 16–17, 1991.*
Berg et al., 1993, Nature 366:695–698, "L–selectin–mediated Lymphocyte Rolling on MAdCAM–1".
Berlin et al., 1993, Cell 74:185–195, "alpha–4–beta–7 Integrin Mediates Lymphocyte Binding to the Mucosal Vascular Addressin MAdCAM–1".
Bonventre and Colvin, 1996, Current Opinion in Nephrology and Hypertension 5:254–261, "Adhesion Molecules in Renal Disease".
Briskin et al., 1993, Nature 363: 461–464, "MAdCAM–1 has Homology to Immunoglobulin and Mucin–like Adhesion Receptors and to IgA1".
Dudley et al., 1995, Genes & Development 9:2795–2807, "A Requirement for Bone Morphogenetic Protein–7 During Development of the Mammalian Kidney and Eye".
Fagotto and Gumbiner, 1996, Developmental Biology 180:445–454, "Cell Contact–Dependent Signaling".
Greve et al., 1989, Cell 56:839–847, "The Major Human Rhinovirus Receptor Is ICAM–1".
Hubank and Schatz, 1994, Nucleic Acids Research 22:5640–5648, "Identifying Differences in mRNA Expression by Representational Difference Analysis of cDNA".
Kaplan et al., 1996, EMBO Journal 15:4282–4296, "Identification of a Surface Glycoprotein on African Green Monkey Kidney Cells as a Receptor for Hepatitis A Virus".
Klinken et al., 1995, Am. J. Physiol. 269:G613–G627, "Mucin Gene Structure and Expression: Protection vs. Adhesion".
Luo et al., 1995, Genes & Development 9:2808–2820, "BMP–7 is an Inducer of Nephrogenesis and is also Required for Eye Development and Skeletal Patterning".
Muller et al., 1997, Cell 88:603–613, "Integrin alpha8–beta1 is Critically Important for Epithelial–Mesenchymal Interactions During Kidney Morphogenesis".
Sastry and Horwitz, 1996, Developmental Biology 180:455–467, "Adhesion–Growth Factor Interactions During Differentiation: An Integrated Biological Response".
Shimizu et al., 1993, Nature 336:630–631, "Mucins in the Mainstream".
Shyjan et al., 1996, J. of Immunology 156:2851–2857, "Human Mucosal Addressin Cell Adhesion Molecule–1 (MAdCAM–1) Demonstrates Structural and Functional Similarities to the alpha–4–beta–7–Integrin Binding Domains of Murine MAdCAM–1, but Extreme Divergence of Mucin–Like Sequences".
Takada et al., 1997, J. Clin. Invest. 99:2682–2690, "The Cytokine–adhesion Molecule Cascade in Ischemia/Reperfusion Injury of the Rat Kidney".
Thadhani et al., 1996, NEJM 334:1448–1460, "Acute Renal Failure".
Weterman et al., 1995, Int. J. Cancer 60;73–81, "nmb, A Novel Gene, is Expressed in Low–Metastatic Human Melanoma Cell Lines and Xenografts".

* cited by examiner

*Primary Examiner*—Patrick J. Nolan
(74) *Attorney, Agent, or Firm*—Biogen, Inc.

(57) ABSTRACT

Proteins which are upregulated in injured or regenerating tissues, as well as the DNA encoding these proteins, are disclosed, as well as therapeutic compositions and methods of treatment encompassing these compounds.

19 Claims, 12 Drawing Sheets

```
   1  GCGGCCGCGTCGACGGTGCCTGTGAGTAAATAGATCAGGGTCTCCTTCAC   50

51  AGCACATTCTCCAGGAAGCCGAGCAAACATTAGTGCTATTTTACCCAGGA  100

101  GGAAATCTAGGTGTAGAGAGCTCTACGGATCTAAGGTTTGGATCTGTACC  150

151  CAGTGCTTTTTTAGGTGTCTTTAGACATTTCTCAGGAAGATGTAGTCTCT  200

201  GTCACCATGTGTGGCTGAATTCTAGCTCAGTCCATCTTATTGTGTTTAAG  250

251  GTAGTTGAAGTTTAGGAACCAACCAGTATGTCTCTGAGCAGAAGAGTACA  300

301  GTGTCCATCTTGAGGACAAGCTCATCTTTACCATTAGAGGGCTGGCCTTG  350

351  GCTTAGATTCTACCGAGAACATACTCTCTAATGGCTGCCCTCAGTTTTCT  400

401  CTGTTTGCTGTCTTATTTGTGTCATGGCCAGAAGTCATATGGATGGCTCT  450

451  ATGTGAGCAAGGACCCAGATAGAAGAGTGTATTTGGGGGAACAGGTTGCC  500

501  CTAACAGAGAGTCCTGTGGGATTCATGCAGTCAGGATGAAGACCTGATCA  550

551  GACAGAGTGTGCTGAGTGCCACGGCTAACCAGAGTGACTTGTCACTGTCC  600

601  TTCAGGTCAACACCATGGTTCAACTTCAAGTCTTCATTTCAGGCCTCCTG  650
                      M   V   Q   L   Q   V   F   I   S   G   L   L

651  CTGCTTCTTCCAGGCTCTGTAGATTCTTATGAAGTAGTGAAGGGGGTGGT  700
       L   L   L   P   G   S   V   D   S   Y   E   V   V   K   G   V   V

701  GGGTCACCCTGTCACAATTCCATGTACTTACTCAACACGTGGAGGAATCA  750
       G   H   P   V   T   I   P   C   T   Y   S   T   R   G   G   I   T

751  CAACGACATGTTGGGGCCGGGGGCAATGCCCATATTCTAGTTGTCAAAAT  800
       T   T   C   W   G   R   G   Q   C   P   Y   S   S   C   Q   N

801  ATACTTATTTGGACCAATGGATACCAAGTCACCTATCGGAGCAGCGGTCG  850
       I   L   I   W   T   N   G   Y   Q   V   T   Y   R   S   S   G   R

851  ATACAACATAAAGGGGCGTATTTCAGAAGGAGACGTATCCTTGACAATAG  900
       Y   N   I   K   G   R   I   S   E   G   D   V   S   L   T   I   E

901  AGAACTCTGTTGATAGTGATAGTGGTCTGTATTGTTGCCGAGTGGAGATT  950
       N   S   V   D   S   D   S   G   L   Y   C   C   R   V   E   I

951  CCTGGATGGTTCAACGATCAGAAAATGACCTTTTCATTGGAAGTTAAACC 1000
       P   G   W   F   N   D   Q   K   M   T   F   S   L   E   V   K   P

1001  AGAAATTCCCACAAGTCCTCCAACAAGACCCACAACTACAAGACCCACAA 1050
       E   I   P   T   S   P   P   T   R   P   T   T   T   R   P   T   T

1051  CCACAAGGCCCACAACTATTTCAACAAGATCCACACATGTACCAACATCA 1100
       T   R   P   T   T   I   S   T   R   S   T   H   V   P   T   S
```

FIG. 1a

| | | |
|---|---|---|
| 1101 | ACCAGAGTCTCCACCTCTACTCCAACACCAGAACAAACACAGACTCACAA | 1150 |
| | T R V S T S T P T P E Q T Q T H K | |
| 1151 | ACCAGAAATCACTACATTTTATGCCCATGAGACAACTGCTGAGGTGACAG | 1200 |
| | P E I T T F Y A H E T T A E V T E | |
| 1201 | AAACTCCATCATATACTCCTGCAGACTGGAATGGCACTGTGACATCCTCA | 1250 |
| | T P S Y T P A D W N G T V T S S | |
| 1251 | GAGGAGGCCTGGAATAATCACACTGTAAGAATCCCTTTGAGGAAGCCGCA | 1300 |
| | E E A W N N H T V R I P L R K P Q | |
| 1301 | GAGAAACCCGACTAAGGGCTTCTATGTTGGCATGTCCGTTGCAGCCCTGC | 1350 |
| | R N P T K G F Y V G M S V A A L L | |
| 1351 | TGCTGCTGCTGCTTGCGAGCACCGTGGTTGTCACCAGGTACATCATTATA | 1400 |
| | L L L L A S T V V V T R Y I I I | |
| 1401 | AGAAAGAAGATGGGCTCTCTGAGCTTTGTTGCCTTCCATGTCTCTAAGAG | 1450 |
| | R K K M G S L S F V A F H V S K S | |
| 1451 | TAGAGCTTTGCAGAACGCAGCGATTGTGCATCCCCGAGCTGAAGACAACA | 1500 |
| | R A L Q N A A I V H P R A E D N I | |
| 1501 | TCTACATTATTGAAGATAGATCTCGAGGTGCAGAATGAGTCCCAGAGGCC | 1550 |
| | Y I I E D R S R G A E | |
| 1551 | TTCTGTGGGGCCTTCTGCCTGGGATTACAGAGATCGTGACTGATTTCACA | 1600 |
| 1601 | GAGTAAAATACCCATTCCAGCTCCTGGGAGATTTTGTGTTTTGGTTCTTC | 1650 |
| 1651 | CAGCTGCAGTGGAGAGGGTAACCCTCTACCCTGTATATGCAAAACTCGAG | 1700 |
| 1701 | GTTAACATCATCCTAATTCTTGTATCAGCAACACCTCAGTGTCTCCACTC | 1750 |
| 1751 | ACTGCAGCGATTCTCTCAAATGTGAACATTTTAGAAGTTTGTGTTTCCTT | 1800 |
| 1801 | TTGTCCATGTAATCATTGGTAATACAAGAATTTTATCTTGTTTATTAAAA | 1850 |
| 1851 | CCATTAATGAGAGGGGAATAGGAATTAAAAGCTGGTGGGAAGGGCCTCCT | 1900 |
| 1901 | GAATTTAGAAGCACTTCATGATTGTGTTTATCTCTTTTATTGTAATTTGA | 1950 |
| 1951 | AATGTTACTTCTATCCTTCCCAAGGGGCAAAATCATGGGAGCATGGAGGT | 2000 |
| 2001 | TTTAATTGCCCTCATAGATAAGTAGAAGAAGAGAGTCTAATGCCACCAAT | 2050 |
| 2051 | AGAGGTGGTTATGCTTTCTCACAGCTCTGGAAATATGATCATTTATTATG | 2100 |
| 2101 | CAGTTGATCTTAGGATGAGGATGGGTTTCTTAGGAGGAGAGGTTACCATG | 2150 |
| 2151 | GTGAGTGGACCAGGCACACATCAGGGGAAGAAAACAATGGATCAAGGGAT | 2200 |
| 2201 | TGAGTTCATTAGAGCCATTTCCACTCCACTTCTGTCTTGATGCTCAGTGT | 2250 |
| 2251 | TCCTAAACTCACCCACTGAGCTCTGAATTAGGTGCAGGGAGGAGACGTGC | 2300 |

FIG. 1b

```
2301  AGAAACGAAAGAGGAAAGAAAGGAGAGAGAGCAGGACACAGGCTTTCTGC  2350
2351  TGAGAGAAGTCCTATTGCAGGTGTGACAGTGTTTGGGACTACCACGGGTT  2400
2401  TCCTTCAGACTTCTAAGTTTCTAAATCACTATCATGTGATCATATTTATT  2450
2451  TTTAAAATTATTTCAGAAAGACACCACATTTTCAATAATAAATCAGTTTG  2500
2501  TCACAATTAATAAAATATTTTGTTTGCTAAGAAGTAAAAAAAAAAAAAAA  2550
2551  AAGTCGACGCGGCCGC  2566
```

FIG. 1c

```
  1  GCGGCCGCGTCGACGGTGCCTGTGAGTAAATAGATCAGGGTCTCCTTCAC   50

51  AGCACATTCTCCAGGAAGCCGAGCAAACATTAGTGCTATTTTACCCAGGA  100

101  GGAAATCTAGGTGTAGAGAGCTCTACGGATCTAAGGTCAACACCATGGTT  150
                                                  M  V

151  CAACTTCAAGTCTTCATTTCAGGCCTCCTGCTGCTTCTTCCAGGCTCTGT  200
      Q  L  Q  V  F  I  S  G  L  L  L  L  P  G  S  V

201  AGATTCTTATGAAGTAGTGAAGGGGGTGGTGGGTCACCCTGTCACAATTC  250
      D  S  Y  E  V  V  K  G  V  V  G  H  P  V  T  I  P

251  CATGTACTTACTCAACACGTGGAGGAATCACAACGACATGTTGGGGCCGG  300
       C  T  Y  S  T  R  G  G  I  T  T  T  C  W  G  R

301  GGGCAATGCCCATATTCTAGTTGTCAAAATATACTTATTTGGACCAATGG  350
      G  Q  C  P  Y  S  S  C  Q  N  I  L  I  W  T  N  G

351  ATACCAAGTCACCTATCGGAGCAGCGGTCGATACAACATAAAGGGGCGTA  400
      Y  Q  V  T  Y  R  S  S  G  R  Y  N  I  K  G  R  I

401  TTTCAGAAGGAGACGTATCCTTGACAATAGAGAACTCTGTTGATAGTGAT  450
      S  E  G  D  V  S  L  T  I  E  N  S  V  D  S  D

451  AGTGGTCTGTATTGTTGCCGAGTGGAGATTCCTGGATGGTTCAACGATCA  500
      S  G  L  Y  C  C  R  V  E  I  P  G  W  F  N  D  Q

501  GAAAATGACCTTTTCATTGGAAGTTAAACCAGAAATTCCCACAAGTCCTC  550
      K  M  T  F  S  L  E  V  K  P  E  I  P  T  S  P  P

551  CAACAAGACCCACAACTACAAGACCCACAACCACAAGGCCCACAACTATT  600
       T  R  P  T  T  T  R  P  T  T  T  R  P  T  T  I

601  TCAACAAGATCCACACATGTACCAACATCAACCAGAGTCTCCACCTCTAC  650
      S  T  R  S  T  H  V  P  T  S  T  R  V  S  T  S  T

651  TCCAACACCAGAACAAACACAGACTCACAAACCAGAAATCACTACATTTT  700
      P  T  P  E  Q  T  Q  T  H  K  P  E  I  T  T  F  Y

701  ATGCCCATGAGACAACTGCTGAGGTGACAGAAACTCCATCATATACTCCT  750
      A  H  E  T  T  A  E  V  T  E  T  P  S  Y  T  P

751  GCAGACTGGAATGGCACTGTGACATCCTCAGAGGAGGCCTGGAATAATCA  800
      A  D  W  N  G  T  V  T  S  S  E  E  A  W  N  N  H

801  CACTGTAAGAATCCCTTTGAGGAAGCCGCAGAGAAACCCGACTAAGGGCT  850
       T  V  R  I  P  L  R  K  P  Q  R  N  P  T  K  G  F

851  TCTATGTTGGCATGTCCGTTGCAGCCCTGCTGCTGCTGCTTGCGAGC    900
       Y  V  G  M  S  V  A  A  L  L  L  L  L  A  S

901  ACCGTGGTTGTCACCAGGTACATCATTATAAGAAAGAAGATGGGCTCTCT  950
       T  V  V  V  T  R  Y  I  I  I  R  K  K  M  G  S  L
```

FIG. 2a

```
 951  GAGCTTTGTTGCCTTCCATGTCTCTAAGAGTAGAGCTTTGCAGAACGCAG  1000
       S  F  V  A  F  H  V  S  K  S  R  A  L  Q  N  A  A
1001  CGATTGTGCATCCCCGAGCTGAAGACAACATCTACATTATTGAAGATAGA  1050
       I  V  H  P  R  A  E  D  N  I  Y  I  I  E  D  R
1051  TCTCGAGGTGCAGAATGAGTCCCAGAGGCCTTCTGTGGGCCTTCTGCCT   1100
       S  R  G  A  E
1101  GGGATTACAGAGATCGTGACTGATTTCACAGAGTAAAATACCCATTCCAG  1150
1151  CTCCTGGGAGATTTTGTGTTTTGGTTCTTCCAGCTGCAGTGGAGAGGGTA  1200
1201  ACCCTCTACCCTGTATATGCAAAACTCGAGGTTAACATCATCCTAATTCT  1250
1251  TGTATCAGCAACACCTCAGTGTCTCCACTCACTGCAGCGATTCTCTCAAA  1300
1301  TGTGAACATTTTAGAAGTTTGTGTTTCCTTTTGTCCATGTAATCATTGGT  1350
1351  AATACAAGAATTTTATCTTGTTTATTAAAACCATTAATGAGAGGGAATA   1400
1401  GGAATTAAAAGCTGGTGGGAAGGGCCTCCTGAATTTAGAAGCACTTCATG  1450
1451  ATTGTGTTTATCTCTTTTATTGTAATTTGAAATGTTACTTCTATCCTTCC  1500
1501  CAAGGGGCAAAATCATGGGAGCATGGAGGTTTTAATTGCCCTCATAGATA  1550
1551  AGTAGAAGAAGAGAGTCTAATGCCACCAATAGAGGTGGTTATGCTTTCTC  1600
1601  ACAGCTCTGGAAATATGATCATTTATTATGCAGTTGATCTTAGGATGAGG  1650
1651  ATGGGTTTCTTAGGAGGAGAGGTTACCATGGTGAGTGGACCAGGCACACA  1700
1701  TCAGGGAAGAAAACAATGGATCAAGGGATTGAGTTCATTAGAGCCATTT   1750
1751  CCACTCCACTTCTGTCTTGATGCTCAGTGTTCCTAAACTCACCCACTGAG  1800
1801  CTCTGAATTAGGTGCAGGGAGGAGACGTGCAGAAACGAAAGAGGAAAGAA  1850
1851  AGGAGAGAGAGCAGGACACAGGCTTTCTGCTGAGAGAAGTCCTATTGCAG  1900
1901  GTGTGACAGTGTTTGGGACTACCACGGGTTTCCTTCAGACTTCTAAGTTT  1950
1951  CTAAATCACTATCATGTGATCATATTTATTTTAAAATTATTTCAGAAAG   2000
2001  ACACCACATTTTCAATAATAAATCAGTTTGTCACAATTAATAAAATATTT  2050
2051  TGTTTGCTAAGAAGTAAAAAGTCGACGCGGCCGC  2084
```

FIG. 2b

```
  1  GCGGCCGCGTCGACTCGCAGGAGGCCGGCACTCTGACTCCTGGTGGATGG   50

51  GACTAGGGAGTCAGAGTCAAGCCCTGACTGGCTGAGGGCGGGCGCTCCGA  100

101  GTCAGCATGGAAAGTCTCTGCGGGGTCCTGGTATTTCTGCTGCTGGCTGC  150
            M  E  S  L  C  G  V  L  V  F  L  L  L  A  A

151  AGGACTGCCGCTCCAGGCGGCCAAGCGGTTCCGTGATGTGCTGGGCCATG  200
      G  L  P  L  Q  A  A  K  R  F  R  D  V  L  G  H  E

201  AGCAGTATCCGGATCACATGAGGGAGAACAACCAATTACGTGGCTGGTCT  250
       Q  Y  P  D  H  M  R  E  N  N  Q  L  R  G  W  S

251  TCAGATGAAAATGAATGGGATGAACAGCTGTATCCAGTGTGGAGGAGGGG  300
      S  D  E  N  E  W  D  E  Q  L  Y  P  V  W  R  R  G

301  AGAGGGCAGATGGAAGGACTCCTGGGAAGGAGGCCGTGTGCAGGCAGCCC  350
      E  G  R  W  K  D  S  W  E  G  G  R  V  Q  A  A  L

351  TAACCAGTGATTCACCGGCCTTGGTGGGTTCCAATATCACCTTCGTAGTG  400
         T  S  D  S  P  A  L  V  G  S  N  I  T  F  V  V

401  AACCTGGTGTTCCCCAGATGCCAGAAGGAAGATGCCAACGGCAATATCGT  450
      N  L  V  F  P  R  C  Q  K  E  D  A  N  G  N  I  V

451  CTATGAGAGGAACTGCAGAAGTGATTTGGAGCTGGCTTCTGACCCGTATG  500
      Y  E  R  N  C  R  S  D  L  E  L  A  S  D  P  Y  V

501  TCTACAACTGGACCACAGGGGCAGACGATGAGGACTGGGAAGACAGCACC  550
      Y  N  W  T  T  G  A  D  D  E  D  W  E  D  S  T

551  AGCCAAGGCCAGCACCTCAGGTTCCCCGACGGGAAGCCCTTCCCTCGCCC  600
       S  Q  G  Q  H  L  R  F  P  D  G  K  P  F  P  R  P

601  CCACGGACGGAAGAAATGGAACTTCGTCTACGTCTTCCACACACTTGGTC  650
       H  G  R  K  K  W  N  F  V  Y  V  F  H  T  L  G  Q

651  AGTATTTTCAAAAGCTGGGTCGGTGTTCAGCACGAGTTTCTATAAACACA  700
        Y  F  Q  K  L  G  R  C  S  A  R  V  S  I  N  T

701  GTCAACTTGACAGTTGGCCCTCAGGTCATGGAAGTGATTGTCTTTCGAAG  750
      V  N  L  T  V  G  P  Q  V  M  E  V  I  V  F  R  R

751  ACACGGCCGGGCATACATTCCCATCTCCAAAGTGAAAGACGTGTATGTGA  800
      H  G  R  A  Y  I  P  I  S  K  V  K  D  V  Y  V  I

801  TAACAGATCAGATCCCTATATTCGTGACCATGTACCAGAAGAATGACCGG  850
       T  D  Q  I  P  I  F  V  T  M  Y  Q  K  N  D  R

851  AACTCGTCTGATGAAACCTTCCTCAGAGACCTCCCCATTTTCTTCGATGT  900
      N  S  S  D  E  T  F  L  R  D  L  P  I  F  F  D  V

901  CCTCATTCACGATCCCAGTCATTTCCTCAACTACTCTGCCATTTCCTACA  950
      L  I  H  D  P  S  H  F  L  N  Y  S  A  I  S  Y  K
```

FIG. 3a

```
 951  AGTGGAACTTTGGGGACAACACTGGCCTGTTTGTCTCCAACAATCACACT  1000
       W  N  F  G  D  N  T  G  L  F  V  S  N  N  H  T

1001  TTGAATCACACGTATGTGCTCAATGGAACCTTCAACTTTAACCTCACCGT  1050
       L  N  H  T  Y  V  L  N  G  T  F  N  F  N  L  T  V

1051  GCAAACTGCAGTGCCGGGACCATGCCCCTCACCCACACCTTCGCCTTCTT  1100
       Q  T  A  V  P  G  P  C  P  S  P  T  P  S  P  S  S

1101  CTTCGACTTCTCCTTCGCCTGCATCTTCGCCTTCACCCACATTATCAACA  1150
       S  T  S  P  S  P  A  S  S  P  S  P  T  L  S  T

1151  CCTAGTCCCTCTTTAATGCCTACTGGCCACAAATCCATGGAGCTGAGTGA  1200
       P  S  P  S  L  M  P  T  G  H  K  S  M  E  L  S  D

1201  CATTTCCAATGAAAACTGCCGAATAAACAGATATGGTTACTTCAGAGCCA  1250
       I  S  N  E  N  C  R  I  N  R  Y  G  Y  F  R  A  T

1251  CCATCACAATTGTAGATGGAATCCTAGAAGTCAACATCATCCAGGTAGCA  1300
       I  T  I  V  D  G  I  L  E  V  N  I  I  Q  V  A

1301  GATGTCCCAATCCCCACACCGCAGCCTGACAACTCACTGATGGACTTCAT  1350
       D  V  P  I  P  T  P  Q  P  D  N  S  L  M  D  F  I

1351  TGTGACCTGCAAAGGGGCCACTCCCACGGAAGCCTGTACGATCATCTCTG  1400
       V  T  C  K  G  A  T  P  T  E  A  C  T  I  I  S  D

1401  ACCCCACCTGCCAGATCGCCCAGAACAGGGTGTGCAGCCCGGTGGCTGTG  1450
       P  T  C  Q  I  A  Q  N  R  V  C  S  P  V  A  V

1451  GATGAGCTGTGCCTCCTGTCCGTGAGGAGAGCCTTCAATGGGTCCGGCAC  1500
       D  E  L  C  L  L  S  V  R  R  A  F  N  G  S  G  T

1501  GTACTGTGTGAATTTCACTCTGGGAGACGATGCAAGCCTGGCCCTCACCA  1550
       Y  C  V  N  F  T  L  G  D  D  A  S  L  A  L  T  S

1551  GCGCCCTGATCTCTATCCCTGGCAAAGACCTAGGCTCCCCTCTGAGAACA  1600
       A  L  I  S  I  P  G  K  D  L  G  S  P  L  R  T

1601  GTGAATGGTGTCCTGATCTCCATTGGCTGCCTGGCCATGTTTGTCACCAT  1650
       V  N  G  V  L  I  S  I  G  C  L  A  M  F  V  T  M

1651  GGTTACCATCTTGCTGTACAAAAAACACAAGACGTACAAGCCAATAGGAA  1700
       V  T  I  L  L  Y  K  K  H  K  T  Y  K  P  I  G  N

1701  ACTGCACCAGGAACGTGGTCAAGGGCAAAGGCCTGAGTGTTTTTCTCAGC  1750
       C  T  R  N  V  V  K  G  K  G  L  S  V  F  L  S

1751  CATGCAAAAGCCCCGTTCTCCCGAGGAGACCGGGAGAAGGATCCACTGCT  1800
       H  A  K  A  P  F  S  R  G  D  R  E  K  D  P  L  L

1801  CCAGGACAAGCCATGGATGCTCTAAGTCTTCACTCTCACTTCTGACTGGG  1850
       Q  D  K  P  W  M  L

1851  AACCCACTCTTCTGTGCATGTATGTGAGCTGTGCAGAAGTACATGACTGG  1900
```

FIG. 3b

```
1901  TAGCTGTTGTTTTCTACGGATTATTGTAAAATGTATATCATGGTTTAGGG  1950
1951  AGCGTAGTTAATTGGCATTTTAGTGAAGGGATGGGAAGACAGTATTTCTT  2000
2001  CACATCTGTATTGTGGTTTTTATACTGTTAATAGGGTGGGCACATTGTGT  2050
2051  CTGAAGGGGGAGGGGGAGGTCACTGCTACTTAAGGTCCTAGGTTAACTGG  2100
2101  GAGAGGATGCCCCAGGCTCCTTAGATTTCTACACAAGATGTGCCTGAACC  2150
2151  CAGCTAGTCCTGACCTAAAGGCCATGCTTCATCAACTCTATCTCAGCTCA  2200
2201  TTGAACATACCTGAGCACCTGATGGAATTATAATGGAACCAAGCTTGTTG  2250
2251  TATGGTGTGTGTGTGTACATAAGATACTCATTAAAAGACAGTCTATTAA   2300
2301  AAA  2303
```

FIG. 3c

```
  1 ATGCATCCTCAAGTGGTCATCTTAAGCCTCATCCTACATCTGGCAGATTC   50
    M  H  P  Q  V  V  I  L  S  L  I  L  H  L  A  D  S

51 TGTAGCTGGTTCTGTAAAGGTTGGTGGAGAGGCAGGTCCATCTGTCACAC  100
    V  A  G  S  V  K  V  G  G  E  A  G  P  S  V  T  L

101 TACCCTGCCACTACAGTGGAGCTGTCACATCAATGTGCTGGAATAGAGGC  150
     P  C  H  Y  S  G  A  V  T  S  M  C  W  N  R  G

151 TCATGTTCTCTATTCACATGCCAAAATGGCATTGTCTGGACCAATGGAAC  200
    S  C  S  L  F  T  C  Q  N  G  I  V  W  T  N  G  T

201 CCACGTCACCTATCGGAAGGACACACGCTATAAGCTATTGGGGGACCTTT  250
    H  V  T  Y  R  K  D  T  R  Y  K  L  L  G  D  L  S

251 CAAGAAGGGATGTCTCTTTGACCATAGAAAATACAGCTGTGTCTGACAGT  300
    R  R  D  V  S  L  T  I  E  N  T  A  V  S  D  S

301 GGCGTATATTGTTGCCGTGTTGAGCACCGTGGGTGGTTCAATGACATGAA  350
    G  V  Y  C  C  R  V  E  H  R  G  W  F  N  D  M  K

351 AATCACCGTATCATTGGAGATTGTGCCACCCAAGGTCACGACTACTCCAA  400
     I  T  V  S  L  E  I  V  P  P  K  V  T  T  T  P  I

401 TTGTCACAACTGTTCCAACCGTCACGACTGTTCGAACGAGCACCACTGTT  450
    V  T  T  V  P  T  V  T  T  V  R  T  S  T  T  V

451 CCAACGACAACGACTGTTCCAACGACAACTGTTCCAACAACAATGAGCAT  500
    P  T  T  T  V  P  T  T  T  V  P  T  T  M  S  I

501 TCCAACGACAACGACTGTTCCGACGACAATGACTGTTTCAACGACAACGA  550
    P  T  T  T  T  V  P  T  T  M  T  V  S  T  T  S

551 GCGTTCCAACGACAACGAGCATTCCAACAACAACAAGTGTTCCAGTGACA  600
    V  P  T  T  T  S  I  P  T  T  T  S  V  P  V  T

601 ACAACGGTCTCTACCTTTGTTCCTCCAATGCCTTTGCCCAGGCAGAACCA  650
    T  T  V  S  T  F  V  P  P  M  P  L  P  R  Q  N  H

651 TGAACCAGTAGCCACTTCACCATCTTCACCTCAGCCAGCAGAAACCCACC  700
     E  P  V  A  T  S  P  S  S  P  Q  P  A  E  T  H  P

701 CTACGACACTGCAGGGAGCAATAAGGAGAGAACCCACCAGCTCACCATTG  750
     T  T  L  Q  G  A  I  R  R  E  P  T  S  S  P  L

751 TACTCTTACACAACAGATGGGAATGACACCGTGACAGAGTCTTCAGATGG  800
    Y  S  Y  T  T  D  G  N  D  T  V  T  E  S  S  D  G

801 CCTTTGGAATAACAATCAAACTCAACTGTTCCTAGAACATAGTCTACTGA  850
    L  W  N  N  N  Q  T  Q  L  F  L  E  H  S  L  L  T

851 CGGCCAATACCACTAAAGGAATCTATGCTGGAGTCTGTATTTCTGTCTTG  900
    A  N  T  T  K  G  I  Y  A  G  V  C  I  S  V  L
```

FIG. 4a

```
901  GTGCTTCTTGCTCTTTTGGGTGTCATCATTGCCAAAAAGTATTTCTTCAA    950
      V  L  L  A  L  L  G  V  I  I  A  K  K  Y  F  F  K

951  AAAGGAGGTTCAACAACTAAGACCCCATAAATCCTGTATACATCAAAGAG   1000
      K  E  V  Q  Q  L  R  P  H  K  S  C  I  H  Q  R  E

```
  1 MHPQVVILSLILHLADSVAGSVKVGGEAGPSVTLPCHYS..GAVTSMCWN  48
    ::  ||.|  :|:|  |::||.:    |  |  .|..||:||  ||   |::|.  ||.
  2 VQLQVFISGLLLLLPGSVDSYEVVKGVVGHPVTIPCTYSTRGGITTTCWG  51

49 RGSCSLFTCQNGIVWTNGTHVTYRKDTRYKLLGDLSRRDVSLTIENTAVS  98
    ||  |..  .|||  ::||||  :||||...||.:  |  :|   ||||||||..  |
 52 RGQCPYSSCQNILIWTNGYQVTYRSSGRYNIKGRISEGDVSLTIENSVDS 101

99 DSGVYCCRVEHRGWFNDMKITVSLEIVPPKVTTTPIVTTVPTVTTVRTST 148
    |||:||||||  .|||||  |:|.|||:  |                           .:.||.
102 DSGLYCCRVEIPGWFNDQKMTFSLEVKP................EIPTSP 135

149 TVPTTTTVPTTTVPTTMSIPTTTTVPTTMTVSTTTSVPTTTSIPTTTSVP 198
    ....|||  ||||  |||:|      |  .|  :..||  .|..|.|.  .|  |    |
136 PTRPTTTRPTTTRPTTIS.....TRSTHVPTSTRVSTSTPTPEQTQTHKP 180

199 VTTTVSTFVPPMPLPRQNHEPVATSPSSPQPAETHPTTLQGAIRREPTSS 248
    .||..                  ||..|.  ...|
181 EITTFYA.........HETTAEVTETP.................. 198

249 PLYSYTTDGNDTVTESSDGLWNNNQTQLFLEHSLLTANTTKGIYAGVCIS 298
       |||..:  :....||::  |||:  ..:  |  ..       |.|||:|.|.:::.
199 ...SYTPADWNGTVTSSEEAWNNHTVRIPLRKP..QRNPTKGFYVGMSVA 243

299 VLVLLALLGVIIAKKY.FFKKEVQQLR...........PHKSCIHQRE 334
    .|:||  |  |.::..:|  :::|.:.  |.           .:  ..:|.|.
244 ALLLLLLASTVVVTRYIIIRKKMGSLSFVAFHVSKSRALQNAAIVHPRA 292
```

FIG. 5

KIDNEY INJURY-RELATED MOLECULES

RELATED APPLICATIONS

This is a continuation-in-part of PCT/US97/09393, filed on May 23, 1997 as a continuation-in-part of U.S. Ser. No. 60/018,228, filed on May 24, 1996 and of U.S. Ser. No. 60/023,442, filed on Aug. 23, 1996. The entire disclosure of each of the aforesaid patent applications are incorporated herein by reference.

FIELD OF THE INVENTION

The invention relates to proteins which are upregulated in injured or regenerating tissues, as well as to the DNA encoding these proteins. The invention further relates to therapeutic compositions and methods of treatment encompassing these proteins.

BACKGROUND OF THE INVENTION

A dynamic remodeling of tissue architecture occurs during development and during tissue repair after injury. Herein are presented results of studies of this process, using a model of kidney injury caused by an ischemia-reperfusion insult.

The kidney is able to repair damage to the proximal tubule epithelium through a complex series of events involving cell death, proliferation of surviving proximal tubule epithelial cells, formation of poorly differentiated regenerative epithelium over the denuded basement membrane, and differentiation of the regenerative epithelium to form fully functional proximal tubule epithelial cells (Wallin et al., Lab. Invest. 66:474–484, 1992; Witzgall et al., Mol. Cell. Biol. 13:1933–1942, 1994; Ichimura et al., Am. J. Physiol. 269: F653–662, 1995; Thadhani et al., N. Engl. J. Med. 334:1448–1460, 1996). Growth factors such as IGF, EGF, and HGF have been implicated in this process of repair, as has the endothelial cell adhesion molecule ICAM-1. However, the mechanisms by which the tubular epithelial cells are restored are still not understood.

To identify molecules involved in processes of injury and repair of the tubular epithelium, differences were analyzed in the mRNA populations between injured/regenerating and normal kidneys using representational difference analysis (RDA). RDA is a PCR-based method for subtraction which yields target tissue or cell specific cDNA fragments by repetitive subtraction and amplification (Hubank and Schutz, Nucl. Acids Res. 22:5640–5648, 1994).

SUMMARY OF THE INVENTION

The invention generally provides Kidney Injury-related Molecules (each of which is henceforth called a "KIM") which are upregulated in renal tissue after injury to the kidney. The KIM proteins and peptides of the invention, as well as their agonists and antagonists, and their corresponding nucleic acids are useful in a variety of therapeutic interventions.

The invention provides a purified and isolated DNA molecule having a nucleotide sequence set forth in SEQ ID NO:1, SEQ ID NO:2, SEQ ID NO:4 or SEQ ID NO:6. The invention also includes the complementary strands of these sequences, DNA molecules which hybridize under stringent conditions to the aforementioned DNA molecules, and DNA molecules which, but for the degeneracy of the genetic code, would hybridize to any of the DNA molecules defined above. These DNA molecules may be recombinant, and may be operably linked to an expression control sequence.

The invention further provides a vector comprising a purified and isolated DNA molecule having a nucleotide sequence set forth in SEQ ID NO:1, SEQ ID NO:2, SEQ ID NO:4 or SEQ ID NO:6, or one of the other DNA molecules defined above. This vector may be a biologically functional plasmid or viral DNA vector. One embodiment of the invention provides a prokaryotic or eukaryotic host cell stably transformed or transfected by a vector comprising a DNA molecule of SEQ ID NO:1, SEQ ID NO:2, SEQ ID NO:4 or SEQ ID NO:6. In another embodiment of the invention, a process is provided for the production of a KIM polypeptide product encoded by a DNA molecule as described above; the process involves growing, under suitable culture conditions, prokaryotic or eukaryotic host cells transformed or transfected with the DNA molecule in a manner allowing expression of the DNA molecule, and recovering the polypeptide product of said expression.

A purified and isolated human KIM protein substantially free of other human proteins is specifically within the invention, as is a process for the production of a polypeptide product having part or all of the primary structural conformation and the biological activity of a KIM protein. KIM proteins of the invention may have an amino acid sequence which comprises SEQ ID NO:3, SEQ ID NO:5, or SEQ ID NO:7, or may be, a variant of SEQ ID NO:3, SEQ ID NO:5 or SEQ ID NO:7, or a purified and isolated protein encoded by the DNA of SEQ ID NO:1, SEQ ID NO:2, SEQ ID NO:4 or SEQ ID NO:6. These proteins can be provided substantially free of other human proteins. The invention further includes variants of these proteins, such as soluble variants or fusion proteins. KIM fusion proteins of the invention may comprise an immunoglobulin, a toxin, an imageable compound or a radionuclide.

The invention also provides a specific antibody, such as a monoclonal antibody (MAb), to the KIM proteins described above. The present antibody binds to any epitope that is unique to a KIM protein disclosed herein. In some embodiments, the epitope is displayed on the surface of a cell expressing KIM. Antigen-binding fragments of the antibody are also provided herein, preferably Fab, Fab2, Fab' and Fv fragments, whether produced by chemical or enzymatic cleavage, or by molecular engineering techniques. Engineered versions of the present antibody include chimeric, humanized and human antibodies, and antibody fusion proteins. Monoclonal antibodies (MAbs) of the present invention can be of mouse, rat, hamster or human origin. An exemplary MAb of the invention is the murine AKG7 MAb disclosed herein, which binds specifically to the human KIM polypeptide disclosed herein. Anti-KIM antibodies of the present invention may be conjugated or fused to a therapeutic agent, toxin, imageable compound or radionuclide. Exemplary therapeutic agents include cytokines, lymphokines, trophic factors, survival factors, chemokines and chemoattractants. Exemplary toxins include ricin and diphtheria toxin. Exemplary imageable compounds include luminescent proteins (e.g., luciferin), fluorescent proteins (e.g., green fluorescent protein), haptens (e.g., biotin), and radioactively labeled proteins. Exemplary radionuclides include any radionuclide used for medical imaging purposes. The invention further encompasses all hybridoma cell lines and engineered host cells which produce antibodies of the invention.

Pharmaceutical compositions are also within the scope of the invention. A pharmaceutical composition of the invention may comprise a therapeutically effective amount of a KIM protein or anti-KIM antibody of the invention, along with a pharmacologically acceptable carrier.

Diagnostic methods are within the invention, such as assessing the presence or course of resolution of renal injury by measuring the concentration of KIM in urine, serum, or urine sediment of patients who have or who are at risk of developing renal disease. Other diagnostic methods that are within the invention include assessing KIM expression level in kidney tissue (e.g., in kidney biopsy tissue) of patients who have, are suspected of having, or are at risk of developing renal cancer (e.g., renal carcinoma). The present methods involve contacting an appropriate tissue or fluid sample derived from the patient being diagnosed, with a KIM antibody or a KIM probe (as the case may be), under binding conditions. Complexes formed by the binding of antibody or probe to KIM protein or nucleic acid (e.g., RNA) in the sample are detected by standard techniques. The presence or abnormal elevation of KIM protein in urine or serum is expected to correlate with renal failure or renal disease. The presence or abnormal elevation of KIM gene expression in renal cells or tissue is expected to correlate with disease processes, particularly carcinogenesis. Such correlations are expected to be useful in the prognostication, staging and clinical management of diseases or other conditions deleterious to renal tissue and/or renal function.

Methods of treatment of the invention include treating patients with therapeutically; effective amounts of KIM, KIM variants, KIM analogs, KIM fusion proteins, KIM agonists, and antibodies to KIM or to KIM ligands. Other therapeutic compounds of the invention include KIM ligands, anti-KIM antibodies, and fusions proteins of KIM ligands. These compounds can be useful in therapeutic methods which either stimulate or inhibit cellular responses that are dependent on KIM function.

Further methods of the invention inhibit the growth of KIM-expressing tumor cells by contacting the cells with a fusion protein of a KIM ligand and either a toxin or radionuclide, or with an anti-KIM antibody conjugated to a toxin or to a radionuclide. Likewise, growth of tumor cells which express KIM ligand may be inhibited by contacting the cells with a fusion protein of a KIM and either a toxin or radionuclide, or with an anti-KIM ligand antibody conjugated to a toxin or to a radionuclide.

The invention also encompasses methods of gene therapy. These include a method of treating a subject with a renal disorder, a method of promoting growth of new tissue in a subject, and a method of promoting survival of damaged tissue in a subject, wherein each method comprises administering to the subject a vector which includes DNA comprising the nucleotide sequence of SEQ ID NO:1, SEQ ID NO:2, SEQ ID NO:4 or SEQ ID NO:6.

The compounds of the invention are also useful for imaging tissues, either in vitro or in vivo. One such method involves targeting an imageable compound to a cell expressing a protein of SEQ ID NO:3, SEQ ID NO:5 or SEQ ID NO:7, comprising contacting the cell with either a monoclonal antibody of the invention or a fusion protein comprising a protein as described above, fused to an imageable compound. For in vivo methods, the cell is within a subject, and the protein or the monoclonal antibody is administered to the subject.

The invention also includes diagnostic methods, such as a method of identifying damage or regeneration of renal cells in a subject, comprising comparing the level of expression of either SEQ ID NO:1, SEQ ID NO:2, SEQ ID NO:4 or SEQ ID NO:6 in renal cells of the subject to a control level of expression of the sequence in control renal cells. Another method of the invention includes identifying upregulation of SEQ ID NO:1, SEQ ID NO:2, SEQ ID NO:4 or SEQ ID NO:6 in cells comprising contacting the cells with an antisense probe and measuring hybridization to RNA within the cell.

A further embodiment of the diagnostic methods of the invention includes assessing the presence or concentration of a molecule of the invention either in urine, serum, or other body fluids, or in urine sediment or tissue samples. The measured injury-related molecule can be correlated with the presence, extent or course of a pathologic process. This correlation can also be used to assess the efficacy of a therapeutic regime.

BRIEF DESCRIPTION OF THE DRAWINGS

FIG. 1 is a text depiction of the nucleotide sequence of rat clone cDNA 3-2 (SEQ ID NO:1), with putative protein reading frame of 615 to 1535. The upper line of the listing is the cDNA sequence (SEQ ID NO: 1), and the lower line is the deduced amino acid sequence (SEQ ID NO: 3).

FIG. 2 is a text depiction of the cDNA sequence of rat clone 1-7 (SEQ ID NO:2), with putative protein reading frame of 145 to 1065. The upper line of the listing is the cDNA sequence (SEQ ID NO: 2), and the lower line is the deduced amino acid sequence (SEQ ID NO:3).

FIG. 3 is a text depiction of the cDNA sequence of rat clone 4-7 (SEQ ID NO: 4), with putative protein reading frame of 107 to 1822. The upper line of the listing is the cDNA sequence (SEQ ID NO: 4), and the lower line is the deduced amino acid sequence (SEQ ID NO:5).

FIG. 4 is a text depiction of the cDNA and deduced amino acid sequences of human clone H13-10-85 (SEQ ID NO: 6); with putative-protein reading frame of 1 to 1002. The upper line of the listing is the cDNA sequence (SEQ ID NO:6), and the lower line is the deduced amino acid sequence (SEQ ID NO:7).

FIG. 5 is a text depiction of a BESTFIT comparison of the amino acid sequence of human clone H13-10-85 (SEQ ID NO:6) with that of rat clone 3-2 (SEQ ID NO:1).

DETAILED DESCRIPTION OF THE INVENTION

Figure 6:
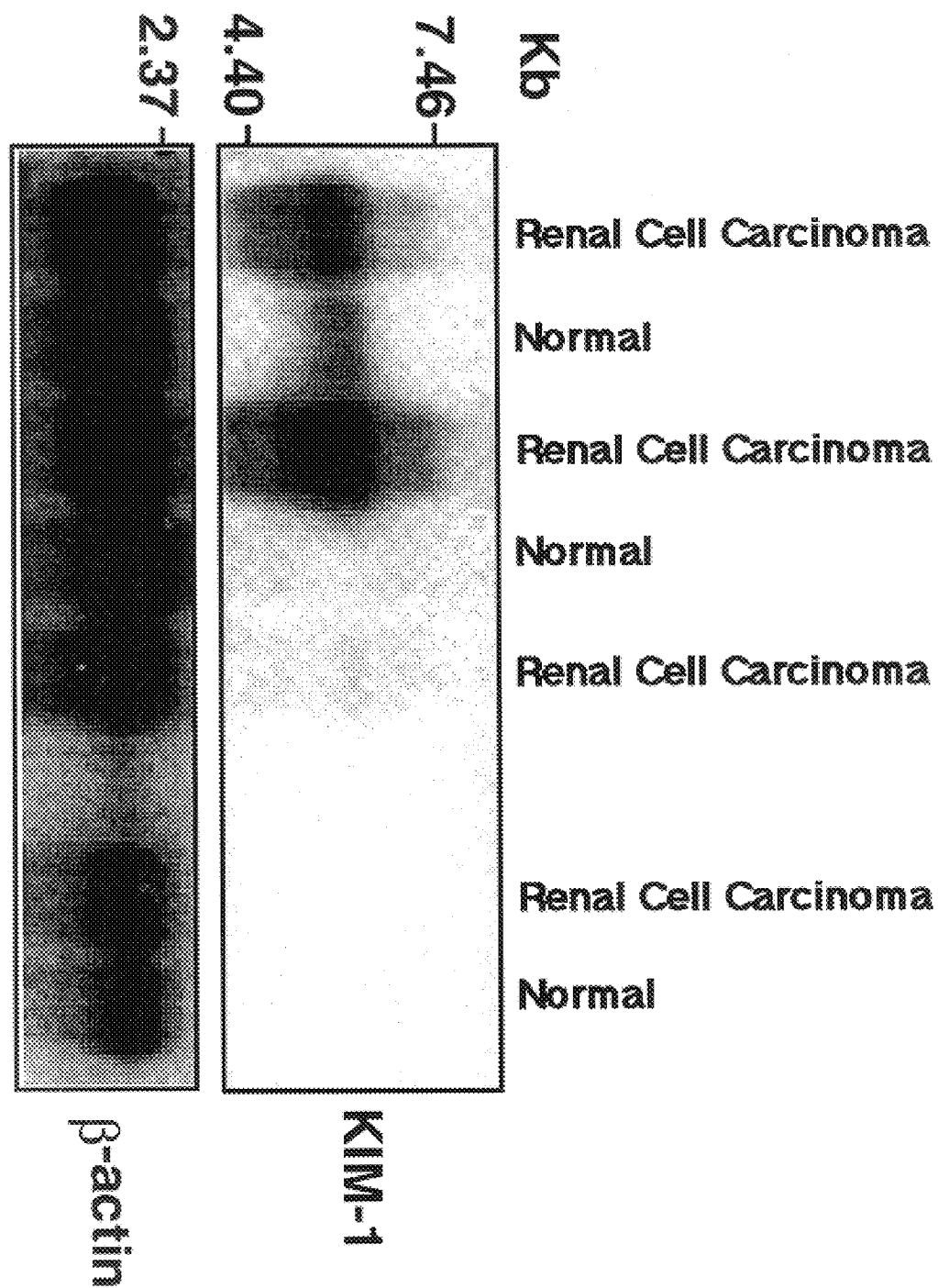
FIG. 6 is a digitized image of a Northern blot of human renal tissue samples isolated from renal carcinomas and from normal renal tissue samples.

KIM genes were identified by analyzing differences in mRNA expression between regenerating and normal kidneys using representational difference analysis (RDA). RDA is a PCR-based method for subtraction which yields target tissue or cell-specific cDNA fragments by repetitive subtraction and amplification. The cDNA representation from 48 hr postischemic adult rat kidney RNA is subtracted with the sample from normal (sham-operated) adult rat kidney. In this procedure, sequences which are common to both postischemic and to normal kidney samples are removed, leaving those sequences which are significantly expressed only in the injured kidney tissue. Such genes encode proteins that may be therapeutically beneficial for renal disorders or involved in the injury process. Several clones have been obtained, sequenced and characterized. The clones are then investigated for their expression patterns during kidney repair, development and tissue distribution by northern analysis and RNA in situ hybridization.

Sequence Identification Numbers

Nucleotide and amino acid sequences referred to in the specification have been given the following sequence identification numbers:

SEQ ID NO:1—nucleotide sequence of rat 3-2 cDNA insert

SEQ ID NO:2—nucleotide sequence of rat 1-7 cDNA insert

SEQ ID NO:3—amino acid sequence of rat KIM-1, encoded by rat 3-2 and 1-7 cDNAs

SEQ ID NO:4—nucleotide sequence of rat 4-7 cDNA insert

SEQ ID NO:5—amino acid sequence encoded by 4-7 cDNA insert

SEQ ID NO:6—nucleotide sequence of human cDNA clone H13-10-85

SEQ ID NO:7—amino acid sequence encoded by human cDNA clone H13-10-85

Definitions of Terms

A "KIM protein", herein used synonymously with "KIM", is a protein encoded by mRNA which is selectively upregulated following injury to a kidney. One group of KIM proteins of interest includes those coded for by mRNA which is selectively upregulated at any time within one week following any insult which results in injury to renal tissue. Examples of times at which such upregulation might be identified include 10 hours, 24 hours, 48 hours or 96 hours following an insult. Examples of types of insults include those resulting in ischemic, toxic or other types of injury.

A "KIM agonist" is a molecule which can specifically trigger a cellular response normally triggered by the interaction of KIM with a KIM ligand. A KIM agonist can be a KIM variant, or a specific antibody to KIM, or a soluble form of the KIM ligand.

A "KIM antagonist" is a molecule which can specifically associate with a KIM ligand or KIM, thereby blocking or otherwise inhibiting KIM binding to the KIM ligand. The antagonist binding blocks or inhibits cellular responses which would otherwise be triggered by ligation of the KIM ligand with KIM or with a KIM agonist. Examples of KIM antagonists include certain KIM variants, KIM fusion proteins and specific antibodies to a KIM ligand or KIM.

A "KIM ligand" is any molecule which noncovalently and specifically binds to a KIM protein. Such a ligand can be a protein, peptide, steroid, antibody, amino acid derivative, or other type molecule, in any form, including naturally-occurring, recombinantly produced, or otherwise synthetic. A KIM ligand can be in any form, including soluble, membrane-bound, or part of a fusion construct with immunoglobulin, fatty acid, or other moieties. The KIM ligand may be an integrin. A membrane-bound KIM ligand can act as a receptor which, when bound to or associated with KIM, triggers a cellular response. In some interactions, KIM may associate with more than a single KIM ligand, or may associate with a KIM ligand as part of a complex with one or more other molecules or cofactors. In a situation where both the KIM and the KIM ligand are bound to cell membranes, the KIM may associate and react with KIM ligand which is bound to the same cell as the KIM, or it may associate and react with KIM ligand be bound to a second cell. Where the KIM ligation occurs between molecules bound to different cells, the two cells may be the same or different with respect to cellular type or origin, phenotypic or metabolic condition, or type or degree of cellular response (e.g., growth, differentiation or apoptosis) to a given stimulus. "KIM ligation" refers to the contact and binding of KIM with a KIM ligand.

By "alignment of sequences" is meant the positioning of one sequence, either nucleotide or amino acid, with that of another, to allow a comparison of the sequence of relevant portions of one with that of the other. An example of one method of this procedure is given in Needleman et al. (J. Mol. Biol. 48:443–453, 1970). The method may be implemented conveniently by computer programs such as the Align program (DNAstar, Inc.). As will be understood by those skilled in the art, homologous or functionally equivalent sequences include functionally equivalent arrangements of the cysteine residues within the conserved cysteine skeleton, including amino acid insertions or deletions which alter the linear arrangement of these cysteines, but do not materially impair their relationship in the folded structure of the protein. Therefore, internal gaps and amino acid insertions in the candidate sequence are ignored for purposes of calculating the level of amino acid sequence similarity or identity between the candidate and reference sequences. One characteristic frequently used in establishing the similarity of proteins is the similarity of the number and location of the cysteine residues between one protein and another.

"Antisense DNA" refers to the sequence of chromosomal DNA that is transcribed.

An "antisense probe" is a probe which comprises at least a portion of the antisense DNA for a nucleic acid portion of interest.

By "cloning" is meant the use of in vitro recombination techniques to insert a particular gene or other DNA sequence into a vector molecule. In order to successfully clone a desired gene, it is necessary to employ methods for generating DNA fragments, for joining the fragments to vector molecules, for introducing the composite DNA molecule into a host cell in which it can replicate, and for selecting the clone having the target gene from amongst the recipient host cells.

By "cDNA" is meant complementary or copy DNA produced from an RNA template by the action of RNA-dependent DNA polymerase (reverse transcriptase). Thus a "cDNA clone" means a duplex DNA sequence complementary to an RNA molecule of interest, carried in a cloning vector.

By "cDNA library" is meant a collection of recombinant DNA molecules containing cDNA inserts which together comprise a representation of the mRNA molecules present in an entire organism or tissue, depending on the source of the RNA templates. Such a cDNA library may be prepared by methods known to those of skill, and described, for example, in Maniatis et al., Molecular Cloning: A Laboratory Manual, supra. Generally, RNA is first isolated from the cells of an organism from whose genome it is desired to clone a particular gene. Preferred for the purposes of the present invention are mammalian, and particularly human, cell lines. Alternatively, RNA may be isolated from a tumor cell, derived from an animal tumor, and preferably from a human tumor. Thus, a library may be prepared from, for example, a human adrenal tumor, but any tumor may be used.

As used herein, the term "DNA polymorphism" refers to the condition in which two or more different nucleotide sequences can exist at a particular site in DNA.

"Expression vector" includes vectors which are capable of expressing DNA sequences contained therein, i.e., the coding sequences are operably linked to other sequences capable of effecting their expression. It is implied, although not always explicitly stated, that these expression vectors must be replicable in the host organisms either as episomes or as an integral part of the chromosomal DNA. A useful, but not a necessary, element of an effective expression vector is a marker encoding sequence, which is a sequence encoding a protein which results in a phenotypic property (such as tetracycline resistance) of the cells containing the protein which permits those cells to be readily identified. In sum, "expression vector" is given a functional definition, and any DNA sequence which is capable of effecting expression of a specified contained DNA code is included in this term, as it is applied to the specified sequence. As at present, such vectors are frequently in the form of plasmids, thus "plasmid" and "expression vector" are often used interchangeably. However, the invention is intended to include such other forms of expression vectors which serve equivalent functions and which may, from time to time become known in the art.

By "functional derivative" is meant the "fragments", "variants", "analogs", or "chemical derivatives" of a molecule. A "fragment" of a molecule, such as any of the antigens of the present invention is meant to refer to any polypeptide subset of the molecule. A "variant" of such molecules is meant to refer to a naturally occurring molecule substantially similar to either the entire molecule, or a fragment thereof. An "analog" of a molecule is meant to refer to a non-natural molecule substantially similar to either the entire molecule or a fragment thereof.

The term "gene" means a polynucleotide sequence encoding a peptide.

By "homogeneous" is meant, when referring to a peptide or DNA sequence, that the primary molecular structure (i.e., the sequence of amino acids or nucleotides) of substantially all molecules present in the composition under consideration is identical.

"Isolated" refers to a protein of the present invention, or any gene encoding any such protein, which is essentially free of other proteins or genes, respectively, or of other contaminants with which it might normally be found in nature, and as such exists in a form not found in nature.

The term "label" refers to a molecular moiety capable of detection including, by way of example, without limitation, radioactive isotopes, enzymes, luminescent agents, and dyes.

The term "probe" refers to a ligand of known qualities capable of selectively binding to a target antiligand. As applied to nucleic acids, the term "probe" refers to a strand of nucleic acid having a base sequence complementary to a target strand.

"Recombinant host cells" refers to cells which have been transformed with vectors constructed using recombinant DNA techniques. As defined herein, the antibody or modification thereof produced by a recombinant host cell is by virtue of this transformation, rather than in such lesser amounts, or more commonly, in such less than detectable amounts, as would be produced by the untransformed host.

By "substantially pure" is meant any protein of the present invention, or any gene encoding any such protein, which is essentially free of other proteins or genes, respectively, or of other contaminants with which it might normally be found in nature, and as such exists in a form not found in nature.

A molecule is said to be "substantially similar" to another molecule if the sequence of amino acids in both molecules is substantially the same, and if both molecules possess a similar biological activity. Thus, provided that two molecules possess a similar activity, they are considered variants as that term is used herein even if one of the molecules contains additional amino acid residues not found in the other, or if the sequence of amino acid residues is not identical. As used herein, a molecule is said to be a "chemical derivative" of another molecule-when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed, for example, in *Remington's Pharmaceutical Sciences*. 16th ed., Mack Publishing Co., Easton, Pa. (1980).

By "vector" is meant a DNA molecule, derived from a plasmid or bacteriophage, into which fragments of DNA may be inserted or cloned. A vector will contain one or more unique restriction sites, and may be capable of autonomous replication in a defined host or vehicle organism such that the cloned sequence is reproducible.

Compounds of the Invention

The invention includes the cDNA of SEQ ID NO: 1, SEQ ID NO:2, SEQ ID NO:4 or SEQ ID NO:6, as well as sequences which include the sequence of SEQ ID NO: 1, SEQ ID NO:2, SEQ ID NO:4, or SEQ ID NO:6, and derivatives of these sequences. The invention also includes vectors, liposomes and other carrier vehicles which encompass these sequence or derivatives of them. The invention further includes proteins transcribed from SEQ ID NO:1, SEQ ID NO:2, SEQ ID NO:4, or SEQ ID NO:6, including but not limited to SEQ ID NO:3, SEQ ID NO:5 or SEQ ID NO:7, and their derivatives and variants.

One embodiment of the invention includes soluble variants of a KIM protein that is usually synthesized as a membrane associated protein, and which is upregulated after injury. Soluble variants lack at least a portion of the transmembrane or intra-membrane section of a native KIM protein. In some examples, the soluble variant lacks the entire transmembrane or intra-membrane section of a native KIM protein. The present soluble variants can be derived from intact or native KIM proteins by any suitable means, including chemical or enzymatic cleavage, or through molecular engineering techniques such by expression of a truncated KIM nucleic acid. Thus, the present soluble variants should be understood to be derivatives of an intact KIM. Soluble variants include fusion proteins which encompass derivatives of KIM proteins that lack at least a portion of the transmembrane or intra-membrane section of a native KIM protein. All types of KIM fusion proteins are included, particularly those which incorporate his-tag, Ig-tag, and myc-tag forms of the molecule. These KIM fusions may have characteristics which are therapeutically advantageous, such as the increased half-life conferred by the Ig-tag. Also included are fusion proteins which incorporate portions of selected domains of the KIM protein.

Variants can differ from naturally occurring KIM protein in amino acid sequence or in ways that do not involve sequence, or both. Variants in amino acid sequence are produced when one or more amino acids in naturally occurring KIM protein is substituted with a different natural amino acid, an amino acid derivative or non-native amino acid. Particularly preferred variants include naturally occurring KIM protein, or biologically active fragments of naturally occurring KIM protein, whose sequences differ from the wild type sequence by one or more conservative amino acid substitutions, which typically have minimal influence on the secondary structure and hydrophobic nature of the protein or peptide. Variants may also have sequences which differ by one or more non-conservative amino acid substitutions, deletions or insertions which do not abolish the KIM protein biological activity. Conservative substitutions typically include the substitution of one amino acid for another with similar characteristics such as substitutions within the following groups: valine, glycine; glycine, alanine; valine, isoleucine; aspartic acid, glutamic acid; asparagine, glutamine; serine, threonine; lysine, arginine; and phenylalanine, tyrosine. The non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid.

Other conservative substitutions can be taken from the table below, and yet others are those which meet the criteria for an accepted point mutation in Dayhoff et al. (1978), 5*Atlas of Protein Sequence and Structure*, Suppl. 3, ch. 22, Natl. Biomed. Res. Found., Washington, D.C. 20007, the teachings of which are incorporated by reference herein.

having an electronegative charge, e.g., glutamic acid or aspartic acid; or (iv) a residue having a bulky side chain, e.g., phenylalanine, is substituted for (or by) one not having such a side chain, e.g., glycine.

The peptides of this invention may also be modified by various changes such as insertions, deletions and substitutions, either conservative or nonconservative where such changes might provide for certain advantages in their use. Splice variants are specifically included in the invention.

In other embodiments, variants with amino acid substitutions which are less conservative may also result in desired derivatives, e.g., by causing changes in charge, conformation and other biological properties. Such substitutions would include for example, substitution of hydrophilic residue for a hydrophobic residue, substitution of a cysteine or proline for another residue, substitution of a residue having a small side chain for a residue having a bulky side chain or substitution of a residue having a net positive charge for a residue having a net negative charge. When the result of a

TABLE 1

CONSERVATIVE AMINO ACID REPLACEMENTS

| For Amino Acid | Code | Replace with any of |
|---|---|---|
| Alanine | A | D-Ala, Gly, beta-Ala, L-Cys, D-Cys |
| Arginine | R | D-Arg, Lys, homo-Arg, D-homo-Arg, Met, D-Met, Ile, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, Beta-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val, Norleu |
| Phenylalanine | F | D-Phe, Tyr, D-Thr, L-Dopa, His, D-His, Trp, D-Trp, Trans 3,4 or 5-phenylproline, cis 3,4 or 5 phenylproline |
| Proline | P | D-Pro, L-I-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), Val, D-Val |
| Threonine | T | D-Thr, Ser, D-Ser, allo-Thr, Met, D-Met, Met)O, D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other variants within the invention are those with modifications which increase peptide stability. Such variants may contain, for example, one or more non-peptide bonds (which replace the peptide bonds) in the peptide sequence. Also included are: variants that include residues other than naturally occurring L-amino acids, such as D-amino acids or non-naturally occurring or synthetic amino acids such as beta or gamma amino acids and cyclic variants. Incorporation of D-instead of L-amino acids into the polypeptide may increase its resistance to proteases. See, e.g., U.S. Pat. No. 5,219,990.

Generally, substitutions that may be expected to induce changes in the functional properties of KIM polypeptides are those in which: (I) a hydrophilic residue, e.g., serine or threonine, is substituted by a hydrophobic residue, e.g., leucine, isoleucine, phenylalanine, or alanine; (ii) a cysteine residue is substituted for (or by) any other residue; (iii) a residue having an electropositive side chain, e.g., lysine, arginine or histidine, is substituted for (or by) a residue given substitution cannot be predicted with certainty, the derivatives may be readily assayed according to the methods disclosed herein to determine the presence or absence of the desired characteristics.

In accordance with the foregoing, the scope of the invention includes proteins and peptides with variant amino acid sequences (sequence variants) having at least eighty percent similarity with a KIM protein. More preferably the sequence similarity is at least ninety percent, or at least ninety-five percent. For example, a sequence variant within the scope of the invention is any which shares at least eighty percent similarity with a KIM selected from rat KIM1 (SEQ ID NO:3) and human KIM1 (SEQ ID NO: 7). The percentage of similarity between a variant sequence and a reference sequence (such as SEQ ID NO:3 or SEQ ID NO: 7) is determined after the variant is aligned with the reference, preferably according to the method of Needelman et al. (1970), 48 J. Mol. Biol. 443–454, or according to an appropriate sequence alignment program (discussed more fully below). The percentage of sequence "identity" of the variant to the reference is the percentage of amino acid or nucleic acid residues of the variant sequence that are identical to the aligned (corresponding) residues of the reference. The percentage of sequence "similarity" is the sum of the percentage of identical corresponding residues and the percentage of variant residues that are conservative substitutions for the aligned (corresponding) reference residues.

A number of algorithms and computer software programs can be utilized to determine whether a sequence of interest is a KIM sequence variant within the scope of this invention. One such is the algorithm of Karlin and Altschul (1990) Proc. Natl. Acad. Sci. USA 87:2264–68, as modified in Karlin and Altschul (1993), Proc. Natl. Acad. Sci. USA 90:5873–77. This algorithm is incorporated into the NBLAST and XBLAST programs of Altschul et al. (1990) J. Mol. Biol. 215:403–10. BLAST nucleotide searches can be performed with NBLAST. BLAST protein searches can be performed with XBLAST. To obtain gapped alignments, gapped BLAST can be utilized as described in Altschul et al. (1997) Nucl. Acids Res. 25(17):3389–3402. All of the foregoing are available through http:\\www.ncbi.nlm.nih.gov. Another suitable algorithm is that of Myers and Miller, CABIOS (1989), which is incorporated into the ALIGN program (version 2.0), which is a part of the Wisconsin Sequence Analysis package of the Genetics Computing Group (GCG). Thus, variants within the invention include any polypeptide or nucleic acid sequence which is identified through BLAST or CABIOS analysis as being related to a KIM nucleic acid or polypeptide sequence disclosed herein (e.g., rat KIM1, SEQ ID NO:3 or human KIM1, SEQ ID NO:7). "Related" sequences are those for which, in the judgement of an ordinarily skilled practitioner, the results of sequence analysis indicate a biologically significant relationship with the reference sequence (e.g., rat KIM1 or human KIM1).

Preferably, sequence variants of the KIM proteins disclosed herein are those having an amino acid sequence which is at least forty (40) percent identical overall (i.e., when aligned) to a disclosed KIM polypeptide sequence, and sharing at least 80% of the aligned KIM cysteine residues. Particularly preferred sequence variants are those which meet the foregoing analysis criteria when analyzed, relative to a KIM reference sequence disclosed herein (e.g., rat KIM1, SEQ ID NO:3 or human KIM1, SEQ ID NO:7), using the program GAP, which is a part of the Wisconsin analysis package of the GCG. To run a GAP analysis, the following program parameters should be used: the gap creation penalty (gap weight) should be set to 3.0, and the gap extension penalty (gap length) should be set to 0.1. GAP uses the algorithm of Needelman et al. (1970), 48 J. Mol. Biol. 443–453, to create an alignment with the largest number of matched (aligned identical) residues and the fewest number of sequence gaps.

Just as it is possible to replace substituents of the scaffold, it is also possible to substitute functional groups which are bound to the scaffold with groups characterized by similar features. These substitutions will initially be conservative, i.e., the replacement group will have approximately the same size, shape, hydrophobicity and charge as the original group. Non-sequence modifications may include, for example, in vivo or in vitro chemical derivatization of portions of naturally occurring KIM protein, as well as changes in acetylation, methylation, phosphorylation, carboxylation or glycosylation.

Also included within the invention are agents which specifically bind to the protein, or a fragment of the protein (SEQ ID NO:3, 5 or 7). These agents include ligands and antibodies (including monoclonal, single chain, double chain, Fab fragments, and others, whether native, human, humanized, primatized, or chimeric). Additional descriptions of these categories of agents are in PCT application 95/16709, the specification of which is herein incorporated by reference.

Experimental Procedures

1. Generation of RNA from Ischemic and Normal Rat Adult Kidneys

Ischemic injured rat kidneys are generated as described by Witzgall et al. (J. Clin Invest. 93: 2175–2188, 1994). Briefly, the renal artery and vein from one kidney of an adult Sprague-Dawley rat are clamped for 40 minutes and then reperfused. Injured kidneys are harvested from the rats at 24 hours and at 48 hours after reperfusion. Kidneys from sham-operated, normal adult Sprague-Dawley rats are also harvested.

Total RNA is prepared from the organs based on the protocol by Glisin et al. (Biochemistry 13: 2633, 1974). Briefly, the harvested organs are placed immediately into GNC buffer (4M guanidine thiocyanate, 0.5% SDS, 25 mM sodium citrate, 0.1% Sigma anti foam) and disrupted on ice with a polytron. Cell debris is removed with a low speed spin in a clinical centrifuge and the supernatant fluid is placed on a 5.7 M CsCl, 25 mM sodium acetate, 1 mM EDTA cushion. RNA is pelleted through the cushion in a SW40Ti rotor at 22K for 15 hrs. RNA is resuspended in sterile DEPC-treated water, precipitated twice with 1/10 volume 3M sodium acetate and 2.5 volumes of EtOH. Poly A+RNA is isolated using an mRNA purification kit (Pharmacia, catalog No.27–9258–02).

2. Representational Difference Analysis (RDA) Method to Isolate 1-7. 3–2 and 4-7 RDA Fragments Double stranded cDNA is synthesized from sham-operated and from 48 hr post-ischemic kidney poly A+RNA using Gibco BRL "Superscript Choices System cDNA Synthesis Kit", catalog No. 18090. First strand is synthesized by priming with oligo dT and using Superscript II™ reverse transcriptase. Second strand is generated using E. coli DNA polymerase I and RNase H followed by T4 DNA polymerase using BRL recommended conditions.

RDA analysis is performed essentially as described by Hubank and Schatz (Nucleic Acid Research 22: 5640–48, 1994). Briefly, 48 hr post-ischemic kidney cDNA is digested with the restriction enzyme Dpn II, and ligated to R-Bgl-12/24 oligonucleotides (see reference for exact sequence). PCR amplification (performed with Perkin-Elmer Taq polymerase and their corresponding PCR buffer) of the linker ligated cDNA is used to generate the initial representation. This PCR product is designated "tester amplicon." The same procedure is used to generate "driver amplicon" from sham-operated rat kidney cDNA.

Hybridization of tester and driver amplicons followed by selective amplification are performed three times to generate Differential Product One (DP1), Two (DP2) and Three (DP3). Generation of the DP1 product is performed as described by Hubank and Schatz (Nucleic Acid Research 22: 5640–48, 1994). The DP2 and DP3 products are also generated as described by Hubank and Schatz (id.), except that the driver:tester ratios are changed to 5,333:1 for DP2 and to 40,000:1 or 4,000:1 for DP3.

Three RDA products are cloned from DP3 into the cloning vector pUC 18: RDA product 1-7 (252 bp) when the DP3 was generated using a ratio of 40,000:1, and product RDA 3-2 (445 bp) and 4-7 (483 bp) when the DP3 was generated using a ratio of 4,000:1. The DNA fragments are subcloned using the Pharmacia Sureclone™ kit (catalog No. 27-9300-01) to repair the ends of the PCR fragments with Klenow enzyme and to facilitate blunt end ligation of the fragments into the pUC18 vector.

3. Northern Analysis

Poly A+RNA (2.5 µg) from rat normal adult kidney (sham operated), from 48 hr post-ischemic injured adult kidney, and from day 18 embryonic kidney is electrophoresed and Northern blotted (Cate, Cell 45:685, 1986) to a Gene-Screen™ membrane (Dupont). Hybridization in PSB buffer (50 mM Tris 7.5, 1M NaCl , 0.1% Na pyrophosphate, 0.2% PVP, 0.2% Ficoll, 0.2% BSA, 1% SDS), containing 10% dextran sulphate and 100 µg/ml tRNA, is performed at 65C using three different probes: 1-7 RDA product, 3-2 RDA product and 4-7 RDA product. All are radiolabeled using Pharmacia's "Ready to Gorm" random priming labeling kit (catalog No.27-9251-01). RDA products 1-7, 3-2 and 4-7 hybridize to mRNAs present in all three samples, but most intensely to mRNAs in the 48 hr post-ischemic kidney RNA samples.

A Northern blot analysis of adult rat tissues indicates that the 1-7 gene is expressed at very low levels in normal adult kidney, testis, spleen and lung. The 3-2 gene is expressed in liver, kidney, spleen, and brain. The 4-7 gene is expressed in spleen, kidney, lung, testis, heart , brain, liver, and skeletal muscle. The presence of different sized mRNAs in some tissues in the 1-7 and 3-2 blot indicates that the primary transcription product of the 1-7 gene and of the 3-2 gene may undergo alternate splicing and/or polyadenylation.

4. Isolation of 3-2 and 4-7 cDNA Clones

A cDNA library is generated from 4 µg of polyA+RNA from 48 hr post-ischemic injured kidney using reagents from BRL Superscript Choice™ System for cDNA synthesis, and Stratagene™ Lambda ZapII cloning kit (catalog No. 236201), according to protocols recommended by the manufacturers.

$10^5$ clones are screened with the 3-2 RDA product as a probe (random primed labeled as described above). Eight positive clones are selected and four are randomly chosen for secondary analysis to obtain pure phage plaques. After tertiary screening, four pure phage clones are isolated. Cloned inserts from the phage are isolated by in vivo excision procedure according to Stratagenem Lambda Zap II kit. The largest insert, of approximately 2.6 kb (referred to as cDNA clone 3-2), is subjected to DNA sequencing. The sequence of the insert (SEQ ID NO:1) is shown in FIG. 1. cDNA clone 3-2 (E. coli K-12, SOLR/p3-2#5-1) has been deposited as ATCC No. 98061. The sequence of cDNA clone 3-2 is identical to that of clone 1-7 cDNA (SEQ ID NO:2), except that nucleotides 136–605 of SEQ ID NO:1 represent an insertion. Thus, SEQ ID NO:2 represents a splice variant form of SEQ ID NO: 1. The clone for 1-7 (E. coli K-12, SOLR/p1-7#3-1) has been deposited as ATCC No. 98060.

$10^5$ clones are screened with the 1-7 RDA product as a probe (random primed radiolabeled as described above). Eight positive clones are selected and four are randomly chosen for secondary analysis to obtain pure phage plaques. After tertiary screening, four pure phage clones are isolated. Cloned inserts from the phage are isolated by in vivo excision procedure according to Stratagene™ Lambda Zap II kit. The largest insert of approximately 2.0 kb (referred to as cDNA clone 1-7) is subjected to DNA sequencing; the sequence of the insert (SEQ ID NO: 2) is shown in FIG. 2.

$10^5$ clones are screened with the 4-7 RDA product as a probe (random primed labeled as described above and hybridized in PSB at 65C). Eight positive clones are selected and four are randomly chosen for secondary analysis to obtain pure phage plaques. After secondary screening, two pure phage clones are isolated. Cloned inserts from the phage are isolated by in vivo excision procedure according to Stratagen™ Lambda Zap II kit. The largest insert, approximately 2.4 kb (referred to as cDNA clone 4-7), is subjected to DNA sequencing. The sequence of the insert, SEQ ID NO: 4, is shown in FIG. 3. The cDNA clone 4-7 (E. coli K-12, SOLR/p4-7#1-1) has been deposited as ATCC No. 98062.

5. Characterization of the 1-7. 3-2 and 4-7 cDNA Clones

A.) DNA and Protein Sequences:

The sequence of 3-2 cDNA (FIG. 1; SEQ ID NO:1) contains an open reading frame of 307 amino acids (FIG. 1; SEQ ID NO:3). A signal sequence of 21 amino acids is inferred from Von Heijne analysis (Von Heijne et al., Nucl. Acid Res. 14:14683 (1986)), and a transmembrane region spanning approximately aa 235–257 indicates that the 3-2 product is a cell surface protein. The sequence of 1–7 cDNA (FIG. 2; SEQ ID NO:2) contains an open reading frame of 307 amino acids, which is identical to the open reading frame contained in the 3-2 cDNA (SEQ ID NO: 3). This 307 amino acid polypeptide is herein designated rat KIM1. The sequence of 4-7 cDNA (FIG. 3; SEQ ID NO:4) contains an open reading frame of 572 amino acids (SEQ ID NO:5). A transmembrane region is located at approximately amino acids 501–521. This 572 amino acid polypeptide is related to the polypeptide known as nmb. Weterman et al. (1995) 60 Int. J. Cancer 73–81.

B.) In situ Analysis of 1-7, 3-2 and 4-7 mRNAs in Contralateral and in Post-ischemic Adult Rat Kidneys:

In situ hybridization is carried out according to the method described by Finch et al., Dev. Dynamics 203: 223–240, 1995. Briefly, both ischemic and contralateral kidneys are perfusion fixed with 4% paraformaldehyde in PBS. Kidneys are further fixed overnight at 4C and processed. Paraffin sections are deparaffinized and rehydrated, fixed with 4% paraformaldehyde in PBS, digested with proteinase K, refixed, then acetylated with acetic anhydride in triethanolamine buffer. Sections are then dehydrated and hybridized with $^{32}$P-labeled riboprobes at 55° C. overnight, with 33P-labeled riboprobes generated from 3-2 RDA or 1-7 RDA products subcloned into BamH1 site of pGEM-11Z. After hybridization, sections were washed under high stringency conditions (2×SSC, 50% formamide at 65° C.). Sections are finally dehydrated, emulsion (NBT-2) coated for autoradiography, and exposed for at least a week. Silver grains are developed and sections are counterstained with toluidine blue and microphotographed.

Analysis of 1-7 and 3-2 mRNA expression by in situ hybridization indicates that these genes are greatly upregulated in damaged kidney cells compared to their expression in normal kidney sections. The expression seen is in regenerative cells of the cortex and outer medulla, most of which appear to be proximal tubule cells.

Analysis of the 4-7 in situ RNA expression pattern also reveals abundant expression of this gene in the injured ischemic kidney compared to the normal adult kidney. The site of expression appears to be infiltrating cells.

6.) Isolation of a Human cDNA Clone Which Cross Hybridizes to the Rat 3-2 cDNA

A $^{32}$P-labeled DNA probe comprising nucleotides 546–969 of the insert of clone 3-2 shown in FIG. 1 is generated and used to screen a human embryonic liver lambda gt10 cDNA library (Clontech Catalog #HL5003a). $1 \times 10^6$ plaques are screened in duplicate using standard conditions as described above but temperature for screening was 55C. For the high stringency wash, the filters are washed in 2×SSC at 55C. Fifty positive phage are identified and plaque purified, and DNA is prepared. The phage DNAs are subjected to Southern analysis using the same probe as above. The Southern blot filter is subjected to a final wash with 0.5×SSC at 55C. Two clones are identified as positive. The insert of clone H13-10-85 is sequenced and a region is found that encodes a protein with a high level of identity to the 3-2 protein shown in FIG. 3.

The nucleotide sequence (SEQ ID NO:6) and predicted amino acid sequence (SEQ ID NO:7) of the human 3-2 related protein are shown in FIG. 4. As shown by the bestfit analysis depicted in FIG. 5, the human 3-2 related protein is 43.8% identical and 59.1% similar to the rat 3-2 protein. Both contain IgG, mucin, transmembrane, and cytoplasmic domains. The six cysteines within the IgG domains of both proteins are conserved. Accordingly, the polypeptide of SEQ ID NO:7 is designated human KIM1 (or KIM-1) herein. It is believed that the mammalian genome (e.g., the human genome) includes genes encoding a family of KIM-1 related proteins. Thus, the human KIM-1 disclosed herein is more precisely designated human KIM-1a.

7) Production of KIM-1 Ig Fusion Protein

A fusion protein of the extracellular domain of KIM and the Fc region of immunoglobulin (Ig) is a useful tool for the study of the molecular and cellular biology of the injured/regenerating kidney and as a therapeutic molecule. To produce Kim Ig fusion protein with the extracellular domain of human and rat KIM-1 protein, a fragment of the extracellular domain of KIM-1 cDNA was amplified by PCR and cloned in the Biogen expression vector, pCA125, for transient expression in COS cells. The expression vector pCA125 produces a fusion protein which has a structure from gene cloned at N-terminus and a human Ig Fc region at the C-terminus. COS cells were transfected with the plasmids SJR 103 or 104; these plasmids express a fusion protein which contains the human KIM sequences 263–1147 (SEQ ID NO:6; SJR 103) or rat KIM sequences 599–1319 (SEQ ID NO:1; SJR 104) of the extracellular domain fused to human Ig Fc region. The cells were grown in 10% FBS in DMEM in the cell factory (Nunc, Naperville, Ill.). Two to three days post-transfection, medium was harvested, concentrated using Amicon concentrator, and fusion protein was purified using Protein-A Sepharose column. After purification, purity of fusion protein was evaluated by SDS-PAGE.

8) Production of Antibodies, Including Monoclonal Antibody (MAb) AKG7, With Binding Specificity for Human KIM Protein Antibody production involves administration of one or more immunogenic doses of a KIM polypeptide preparation (whether isolated, or as part of a cell suspension, fraction or extract) to an appropriate non-human animal, such as a mouse, rat, rabbit, gunea pig, turkey, goat, sheep, pig or horse. To enhance immunogenicity, the preparation is emulsified with a conventional adjuvant (e.g., Complete Freund's Adjuvant, CFA). Serum immunoglobulins (Ig), using peripheral blood samples withdrawn at intervals (e.g., weekly) after initial or a subsequent immunization, are monitored to detect the onset and/or maturation of a humoral immune response to KIM. Any conventional technique, e.g., ELISA, RIA, Western blotting, or the like, can be used to detect and/or quantitate (titer) the KIM-specific Ig. High titer immune sera are preferred for use as anti-KIM polyclonal antibodies herein. High titer sera (e.g., having a titer of at least 1:1000) can be harvested in bulk for purification of anti-anti-KIM Ig, using conventional immunoaffinity chromatography (e.g., using a Protein A resin).

Animals (e.g., mice, rats, guinea pigs, hamsters) having a high serum titer of anti-KIM Ig also can be used for the conventional production of monoclonal antibodies (MAb) with binding specificity for KIM. Splenocytes are isolated from such animals and are fused with a myeloma cell line according to standard techniques to produce hybridomas. Such hybridomas are cloned by limiting dilution, fluorescence-activated cell sorting, or any other suitable cell isolation technique, to produce monoclonal hybridoma cell lines of the present invention. Hybridoma lines of the present invention are useful for the production of anti-KIM MAbs, and also as sources from which nucleic acids encoding the present anti-KIM MAbs can be routinely isolated. Such nucleic acids, encoding heavy and/or light chain polypeptides of the present MAbs, can be used to produce recombinant, engineered versions of the present MAbs, including truncated MAb polypeptides, chimeric or humanized MAbs, and MAb fusion proteins.

By way of illustration, mice have been immunized with a human KIM1-Ig fusion protein as disclosed herein, which was immobilized on Protein A Sepharose beads and emulsified in CFA. The fusion protein included the extracellular domain of human KIM1 (amino acids 1 to 291) fused to a truncated human IgG1 polypeptide comprising the hinge-C2–C3 domains of the IgG1 heavy chain polypeptide. The onset and maturation of a humoral immune response was monitored using a conventional ELISA, in which another Ig fusion protein was used as a blocking agent to subtract serum Ig's having undesired specificity for the IgG1 portion of the KIM1 fusion protein. Following conventional isolation of immune splenocytes, fusion, ELISA screening, and cloning by limiting dilution, ten MAbs were obtained with desirable binding specificity for human KIM 1. Among these, one, designated AKG7, is preferred herein. The AKG7 antibody is useful in ELISA, Western blot and immunohistochemistry analysis of human KIM1 polypeptides. The present technique can be repeated and/or adapted routinely to produce any number of MAbs to domains (e.g., the extracellular domain) of KIM proteins, that have the KIM-specific binding properties of MAb AKG7 and are useful in the analytical, diagnostic and therapeutic methods described herein.

MAbs of the present invention, such as AKG7, are obtained from cell culture media conditioned by the present hybridoma lines, or from ascites fluid, or from media conditioned by an engineered host cell expressing a heavy and/or light chain nucleic acid construct encoding an anti-KIM MAb of the present invention. Such MAbs are purified using conventional immunoaffinity chromatography, and used in the various diagnostic, analytical and therapeutic methods described herein.

Diagnostic Uses of the Compounds of the Invention

Anti-KIM antibodies of the invention, which specifically bind to the protein of SEQ ID NO:3, SEQ ID NO:5 or SEQ ID NO:7 or a fragment thereof, are useful in several diagnostic methods. These agents may be labeled with detectable markers, such as fluoroscopically or radiographically opaque substances, and administered to a subject to allow imaging of tissues which express KIM protein. The agents may also be bound to substances, such as horseradish peroxidase, which can be used as immunocytochemical stains to allow visualization of areas of KIM protein-positive cells on histological sections. A specific antibody could be used alone in this manner, and sites where it is bound can be visualized in a sandwich assay using an anti-immunoglobulin antibody which is itself bound to a detectable marker.

For example and not by way of limitation, the AKG7 MAb can be used to visualize cells producing KIM-1 protein in immunohistochemistry analysis of human renal tissue samples. Immunohistochemistry is carried out on paraformaldehyde-fixed paraffin sections by deparaffinizing the sections, then ablating endogenous peroxidase activity by incubation in 2% hydrogen peroxide in methanol for 20 min. Sections are then heated in a microwave oven in 0.1 M citrate buffer, pH 6.0, for 10 min., then blocked with diluted goat serum (1:67) overnight at 4° C. Thereafter, sections are incubated with affinity purified AKG7 or control IgG at a concentration of 5 µg/mL. After 1 hr, the sections are washed in PBS and incubated with biotinylated goat anti-mouse IgG for 30 min. After further washes with PBS, the sections are incubated with avidin-biotinylated horseradish peroxidase complex (Vectastain Elite ABC kit, Vector Laboratories) for 1 hr. Sections are washed in PBS and developed by the addition of 50 mM sodium phosphate buffer, pH 7.6, containing 0.12% 3,3-diaminobenzidine tetrahydrochloride (Sigma), 0.0075% nickel chloride, 0.0075% cobalt chloride, and 0.0075% hydrogen peroxide for 2–5 min., producing a dark brown stain indicating immunoreactivity. Sections are then counterstained with 0.01% toluidine blue. This technique has been used to visualize KIM-1 immunoreactivity in paraffin sections from two different human patients with renal cell carcinoma. Sections comprising tumor tissue and adjacent normal renal tissue were assessed. In patients, strong KIM-1 immunoreactivity was noted in tumor tissue. By contract, immunoreactivity was virtually absent in adjacent normal tissue (as judged by pathology). Immunoreactivity was also virtually absent in normal control renal tissue sections. These data are consistent with the utility of antibodies to KIM-1 as reagents for the diagnosis, prognostication and/or staging of renal cancers.

Specific antibodies to KIM protein are also useful in immunoassays to measure KIM presence or concentration in samples of body tissues and fluids. Such concentrations may be correlated with different disease states. As an embodiment of particular interest, the invention includes a method of diagnosing renal injury, or of monitoring a process of renal repair, by measuring the concentration of KIM or of KIM fragments in the urine, plasma or serum of a patient. Similarly, KIM can be measured in urine sediment, in particular in cellular debris in the urine sediment. Casts of renal tubule cells, which may be present in urine sediment from patients with ongoing renal disease, may contain elevated levels of KIM protein and nRNA.

Specific antibodies to KIM protein may also be bound to solid supports, such as beads or dishes, and used to remove the ligand from a solution, either for measurement, or for purification and characterization of the protein or its attributes (such as posttranslational modifications). Such characterization of a patient's KIM protein might be useful in identifying deleterious mutants or processing defects which interfere with KIM function and are associated with abnormal patient phenotypes. Each of these techniques is routine to those of skill in the immunological arts.

Additional imaging methods utilize KIM or KIM fragments, fused to imageable moieties, for diagnostic imaging of tissues that express KIM ligands, particularly tumors.

Further diagnostic techniques are based on demonstration of upregulated KIM mRNA in tissues, as an indication of injury-related processes. This technique has been tested and found workable in a model of ischemic injury in rats, as follows.

To determine if the amount of KIM-1 protein is increased after injury, kidney homogenates of contralateral and postischemic kidneys were examined 24 and 48 hours following a 40 minute clamping of the renal artery and vein of a single kidney for each rat. The kidney homogenate was assessed for the presence of KIM-1 protein. Western blot analysis identifies three proteins detected by two different antibodies after ischemic injury, which are not detectable in homogenates from contralateral kidneys which were not exposed to ischemic injury. The apparent molecular weights of the bands are approximately 40 kDa, 50 kDa and 70–80 kDa. The three protein species detected by western blotting could represent glycosylated forms of the same protein given the presence of potential N and O linked glycosylation sites. The fact that each of these proteins react with two different sets of polyclonal antibodies supports the idea that they are related to KIM-1 and are not cross-reacting bands. Confirmation of this prediction came from the results of partial CNBr cleavage of the three proteins which revealed they shared common CNBr cleavage fragments. Since the cytoplasmic domain of the KIM-1 protein is not predicted to contain any major post-translational modifications, the two smallest products of the digest (4.7 kDa and 7.4 kDa) detected with antibodies directed against the cytoplasmic domain of KIM-1 should be the same size for the three different KIM-1 protein bands if they originate from the same protein. The KIM1 40 kDa and 70–80 kDa proteins indeed produced fragments migrating at the predicted size. Digest of the 50 kDa protein band gave also the same C-terminal signature band peptide.

The KIM-1 sequence presents two putative sites for N-glycosylation and a mucin domain where O-glycosylation could cover the polypeptide chain. The three KIM-1 bands detected in postischemic kidney could correspond to glycosylation variants of the same core protein. De-N-glycosylation with PNGase F resulted in a shift of all three bands to a lower molecular weight, corresponding to a loss of about 3 kDa, indicating that all three proteins are N-glycosylated. Differences in O-glycosylation might explain the differences in sizes of these three bands.

Further studies are expected to corroborate the correlation between KIM-1 expression and disease status of renal tissue. For example and not by way of limitation, Northern blot analysis can be carried out to establish levels of KIM-1 expression in normal and cancerous renal tissue samples. Poly(A)+RNA is obtained from tissue samples of interest (e.g., kidney biopsy or necropsy samples, or control samples), size fractionated by electrophoresis, and transferred to a GeneScreen membrane (NEN Life Science Products). Hybridization with a KIM-1 probe corresponding to part or all of the open reading frame of the KIM-1 gene of interest (e.g., human KIM-1, SEQ ID NO:6) is carried out in plaque screening buffer (PSB, 50 mM Tris, pH 7.5, 1 M NaCl, 0.1% sodium pyrophosphate, 0.2% polyvinylpyrrolidone, 0.2% Ficoll, 0.2% bovine serum albumin, 1% SDS) containing 10% dextran sulfate and 100 µg/mL tRNA at 65° C. The KIM-1 probe is preferably detectably labeled, e.g., radiolabelled. The membrane is then washed to remove unbound probe, and KIM-1 mRNA is visualized using standard membrane development techniques. Thereafter, the KIM-1 probe is stripped from the blot, and the blot is rehybridized with a control probe, such as a β-actin probe.

The results of an exemplary Northern blot analysis are set forth in FIG. 6: biopsy samples containing histologically normal renal tissue were compared to renal tumor tissues (renal cell carcinoma) obtained from four different patients afflicted with renal cancers. KIM-1 expression was virtually undetectable in three of the four normal samples and was weakly detectable in the fourth. In contract, two of the four renal cancer samples displayed strong KIM-1 expression. These results are consistent with the utility of KIM-1 probes as reagents for the diagnosis, prognostication or staging of renal cancers. Without being limited hereby, it is believed that aberrant KIM-1 gene expression may correlate with the degree of neoplastic transformation, agressiveness or metastatic propensity of a given renal cell carcinoma. Thus, assessment of KIM-1 gene expression is believed to provide information useful in conjunction with other, conventional diagnostic and/or clinical criteria for characterizing renal cancers.

Therapeutic Uses of the Compounds of the Invention

The therapeutic methods of the invention involve selectively promoting or inhibiting cellular responses that are dependent on KIM ligation. Where the KIM and the KIM ligand are both membrane bound, and expressed by different cells, the signal transduction may occur in the KIM-expressing cell, in the KIM ligand-expressing cell, or in both.

KIM ligation-triggered response in a KIM ligand-expressing cell may be generated by contacting the cell with exogenous KIM, KIM fusion proteins or activating antibodies against KIM ligand, either in vitro or in vivo. Further, responses of the KIM ligand-expressing cell that would otherwise be triggered by endogenous KIM could be blocked by contacting the KIM ligand-expressing cell with a KIM ligand antagonist (e.g., an antagonist antibody that binds to KIM ligand), or by contacting the endogenous KIM with an anti-KIM antibody or other KIM-binding molecule which prevents the effective ligation of KIM with a KIM ligand.

Similarly, the responses triggered by KIM ligation in the KIM-expressing cell may be promoted or inhibited with exogenous compounds. For example, KIM ligation-triggered response in a KIM-expressing cell may be generated by contacting the cell with a soluble KIM ligand, or certain anti-KIM activating antibodies. Further, responses of the KIM-expressing cell that would otherwise be triggered by interaction with endogenous KIM ligand could be blocked by contacting the KIM-expressing cell with an antagonist to KIM (e.g., a blocking antibody that binds to KIM in a manner that prevents effective, signal-generating KIM ligation), or by contacting the endogenous KIM ligand with an anti-KIM ligand antibody or other KIM ligand-binding molecule which prevents the effective ligation of KIM with the KIM ligand.

Which of the interventions described above are useful for particular therapeutic uses depend on the relevant etiologic mechanism of either the pathologic process to be inhibited, or of the medically desirable process to be promoted, as is apparent to those of skill in the medical arts. For example, where KIM ligation results in desirable cellular growth, maintenance of differentiated phenotype, resistance to apoptosis induced by various insults, or other medically advantageous responses, one of the above-described interventions that promote ligation-triggered response may be employed. In the alternative, one of the inhibitory interventions may be useful where KIM ligation invokes undesirable consequences, such as neoplastic growth, deleterious loss of cellular function, susceptibility to apoptosis, or promotion of inflammation events.

Following are examples of the previously described therapeutic methods of the invention. One therapeutic use of the KIM-related compounds of the invention is for treating a subject with renal disease, promoting growth of new tissue in a subject, or promoting survival of damaged tissue in a subject, and includes the step of administering to the subject a therapeutically effective amount of a KIM protein of the invention, or of a pharmaceutical composition which includes a protein of the invention. The protein used in these methods may be a fragment of a full-length KIM protein, a soluble KIM ligand protein or fusion fragment, or a KIM agonist. These methods may also be practiced by administering to the subject a therapeutically effective amount of an agonist antibody of the invention, or a pharmaceutical composition which includes an agonist antibody of the invention. A KIM protein may be administered concurrently with a therapeutically effective amount of a second compound which exerts a medically desirable adjunct effect. While tissues of interest for these methods may include any tissue, preferred tissues include renal tissue, liver, neural tissue, heart, stomach, small intestine, spinal cord, or lung. Particular renal conditions which may be beneficially treated with the compounds of the invention include acute renal failure, acute nephritis, chronic renal failure, nephrotic syndrome, renal tubule defects, kidney transplants, toxic injury, hypoxic injury, and trauma. Renal tubule defects include those of either hereditary or acquired nature, such as polycystic renal disease, medullary cystic disease, and medullary sponge kidney. This list is not limited, and may include many other renal disorders (see, e.g., Harrison's Principles of Internal Medicine, 13th ed., 1994, which is herein incorporated by reference.) The subject of the methods may be human.

A therapeutic intervention for inhibiting growth of undesirable, KIM ligand-expressing tissue in a subject includes the step of administering to the subject a therapeutically effective amount of a KIM antagonist (e.g., an antagonist antibody that binds to KIM ligand), or by administering a therapeutically effective amount of an anti-KIM antibody or other KIM-binding molecule which blocks KIM binding to the KIM ligand-expressing tissue. In an embodiment of interest, the KIM antagonist or anti-KIM antibody may be used therapeutically to inhibit or block growth of tumors which depend on KIM protein for growth.

Other methods of the invention include killing KIM ligand-expressing tumor cells, or inhibiting their growth, by contacting the cells with a fusion protein of a KIM and a toxin or radionuclide, or an anti-KIM ligand antibody conjugated to a toxin or radionuclide. The cell may be within a subject, and the protein or the conjugated antibody is administered to the subject.

Also encompassed within the invention is a method for targeting a toxin or radionuclide to a cell expressing a KIM, comprising contacting the cell with a fusion protein comprising a KIM ligand and a toxin or radionuclide, or an anti-KIM antibody conjugated to a toxin or radionuclide. Another embodiment includes the method of suppressing growth of a tumor cell which expresses KIM, comprising contacting the cell with a fusion protein of KIM ligand and a toxin or radionuclide or with an anti-KIM antibody conjugated to a toxin or radionuclide; the cell may be within a subject, and the protein administered to the subject.

The term "subject" used herein is taken to mean any mammal to which KIM may be administered. Subjects specifically intended for treatment with the method of the invention include humans, as well as nonhuman primates, sheep, horses, cattle, goats, pigs, dogs, cats, rabbits, guinea pigs, hamsters, gerbils, rats and mice, as well as the organs, tumors, and cells derived or originating from these hosts.

Use of Compounds of the Invention in Gene Therapy

The KIM genes of the invention are introduced into damaged tissue, or into tissue where stimulated growth is desirable. Such gene therapy stimulates production of KIM protein by the transfected cells, promoting cell growth and/or survival of cells that express the KIM protein.

In a specific embodiment of a gene therapy method, a gene coding for a KIM protein may be introduced into a renal target tissue. The KIM protein would be stably expressed and stimulate tissue growth, division, or differentiation, or could potentiate cell survival. Furthermore, a KIM gene may be introduced into a target cell using a variety of well-known methods that use either viral or non-viral based strategies.

Non-viral methods include electroporation, membrane fusion with liposomes, high velocity bombardment with DNA-coated microprojectiles, incubation with calcium-phosphate-DNA precipitate, DEAE-dextran mediated transfection, and direct micro-injection into single cells. For instance, a KIM gene may be introduced into a cell by calcium phosphate coprecipitation (Pillicer et al., Science, 209: 1414–1422 (1980); mechanical microinjection and/or particle acceleration (Anderson et al., Proc. Nat. Acad. Sci. USA, 77: 5399–5403 (1980); liposome based DNA transfer (e.g., LIPOFECTIN-mediated transfection-Fefgner et al., Proc. Nat. Acad. Sci., USA, 84: 471–477,1987; Gao and Huang, Biochim. Biophys. Res. Comm., 179: 280–285, 1991; DEAE Dextran-mediated transfection; electroporation (U.S. Pat. No. 4,956,288); or polylysine-based methods in which DNA is conjugated to deliver DNA preferentially to liver hepatocytes (Wolff et al., Science, 247: 465–468, 1990; Curiel et al., Human Gene Therapy 3: 147–154, 1992).

Target cells may be transfected with the genes of the invention by direct gene transfer. See, e.g., Wolff et al., "Direct Gene Transfer Into Moose Muscle In Vivo", Science 247:1465–68, 1990. In many cases, vector-mediated transfection will be desirable. Any of the methods known in the art for the insertion of polynucleotide sequences into a vector may be used. (See, for example, Sambrook et al., Molecular Cloning: A Laboratory Manual, Cold Spring Harbor Laboratory, Cold Spring Harbor, N.Y., 1989; and Ausubel et al., Current Protocols in Molecular Biology, J. Wiley & Sons, NY, 1992, both of which are incorporated herein by reference.) Promoter activation may be tissue specific or inducible by a metabolic product or administered substance. Such promoters/enhancers include, but are not limited to, the native c-ret ligand protein promoter, the cytomegalovirus immediate-early promoter/enhancer (Karasuyama et al., J. Exp. Med., 169: 13,1989); the human beta-actin promoter (Gunning et al., Proc. Nat. Acad. Sci. USA, 84: 4831,1987; the glucocorticoid-inducible promoter present in the mouse mammary tumor virus long terminal repeat (MMTV LTR) (Klessig et al., Mol. Cell. Biol., 4: 1354, 1984); the long terminal repeat sequences of Moloney murine leukemia virus (MuLV LTR) (Weiss et al., RNA Tumor Viruses, Cold Spring Harbor Laboratory, Cold Spring Harbor, N.Y., 1985); the SV40 early region promoter (Bernoist and Chambon, Nature, 290:304,1981); the promoter of the Rous sarcoma virus (RSV) (Yamamoto et al., Cell, 22:787, 1980); the herpes simplex virus (HSV) thymidine kinase promoter (Wagner et al., Proc. Nat. Acad. Sci. USA, 78: 1441, 1981); the adenovirus promoter (Yamada et al., Proc. Nat. Acad. Sci. USA, 82: 3567, 1985).

The KIM genes may also be introduced by specific viral vectors for use in gene transfer systems which are now well established. See for example: Madzak et al., J. Gen. Virol., 73: 1533–36, 1992 (papovavirus SV40); Berkner et al., Curr. Top. Microbiol. Immunol., 158: 39–61, 1992 (adenovirus); Hofmann et al., Proc. Natl. Acad. Sci. 92: 10099–10103, 1995 (baculovirus); Moss et al., Curr. Top. Microbiol. Immunol., 158: 25–38,1992 (vaccinia virus); Muzyczka, Curr. Top. Microbiol. Immunol., 158: 97–123, 1992 (adeno-associated virus); Margulskee, Curr. Top. Microbiol. Immunol., 158: 67–93, 1992 (herpes simplex virus (HSV) and Epstein-Barr virus (HBV)); Miller, Curr. Top. Microbiol. Immunol., 158: 1–24, 1992 (retrovirus); Brandyopadhyay et al.,Mol. Cell. Biol., 4: 749–754, 1984 (retrovirus); Miller et al., Nature, 357: 455–450, 1992 (retrovirus); Anderson, Science, 256: 808–813, 1992 (retrovirus), Current Protocols in Molecular Biology: Sections 9.10–9.14 (Ausubel et al., Eds.), Greene Publishing Associcates, 1989, all of which are incorporated herein by reference.

Preferred vectors are DNA viruses that include adenoviruses (preferably Ad-2 or Ad-5 based vectors), baculovirus, herpes viruses (preferably herpes simplex virus based vectors), and parvoviruses (preferably "defective" or non-autonomous parvovirus based vectors, more preferably adeno-associated virus based vectors, most preferably AAV-2 based vectors). See, e.g., Ali et al., Gene Therapy 1: 367–384, 1994; U.S. Pat. Nos. 4,797,368 and 5,399,346 and discussion below.

The choice of a particular vector system for transferring, for instance, a KIM sequence will depend on a variety of factors. One important factor is the nature of the target cell population. Although retroviral vectors have been extensively studied and used in a number of gene therapy applications, they are generally unsuited for infecting cells that are not dividing but may be useful in cancer therapy since they only integrate and express their genes in replicating cells. They are useful for ex vivo approaches and are attractive in this regard due to their stable integration into the target cell genome.

Adenoviruses are eukaryotic DNA viruses that can be modified to efficiently deliver a therapeutic or reporter transgene to a variety of cell types. The general adenoviruses types 2 and 5 (Ad2 and Ad5, respectively), which cause respiratory disease in humans, are currently being developed for gene therapy of Duchenne Muscular Dystrophy (DMD) and Cystic Fibrosis (CF). Both Ad2 and Ad5 belong to a subclass of adenovirus that are not associated with human malignancies. Adenovirus vectors are capable of providing extremely high levels of transgene delivery to virtually all cell types, regardless of the mitotic state. High titers ($10^{13}$ plaque forming units/ml) of recombinant virus can be easily generated in 293 cells (an adenovirus-transformed, complementation human embryonic kidney cell line: ATCC CRL1573) and cryo-stored for extended periods without appreciable losses. The efficacy of this system in delivering a therapeutic transgene in vivo that complements a genetic imbalance has been demonstrated in animal models of various disorders. See Watanabe, Atherosclerosis, 36: 261–268, 1986; Tanzawa et al., FEBS Letters 118(1):81–84, 1980; Golasten et al., New Engl.J. Med. 309:288–296, 1983; Ishibashi et al., J. Clin. Invest. 92: 883–893, 1993; and Ishibashi et al., J. Clin. Invest. 93: 1889–1893, 1994, all of which are incorporated herein by reference. Indeed, recombinant replication defective adenovirus encoding a cDNA for the cystic fibrosis transmembrane regulator (CFTR) has been approved for use in at least two human CF clinical trials. See, e.g., Wilson, Nature 365:691–692, 1993. Further support of the safety of recombinant adenoviruses for gene therapy is the extensive experience of live adenovirus vaccines in human populations.

The first-generation recombinant, replication-deficient adenoviruses which have been developed for gene therapy of DMD and other inherited disorders contain deletions of the entire E1a and part of the E1b regions. This replication-defective virus is grown in 293 cells containing a functional adenovirus E1a gene which provides a transacting E1a protein. E1-deleted viruses are capable of replicating and producing infectious virus in the 293 cells, which provide E1a and E1b region gene products in trans. The resulting virus is capable of infecting many cell types and can express the introduced gene (providing it carries its own promoter), but cannot replicate in a cell that does not carry the E1 region DNA unless the cell is infected at a very high multiplicity of infection. Adenoviruses have the advantage that they have a broad host range, can infect quiescent or terminally differentiated cells such as neurons, and appear essentially non-oncogenic. Adenoviruses do not appear to integrate into the host genome. Because they exist extrachromasomally, the risk of insertional mutagenesis is greatly reduced. Ali et al., supra, at 373. Recombinant adenoviruses (rAdV) produce very high titers, the viral particles are moderately stable, expression levels are high, and a wide range of cells can be infected. Their natural host cells are airway epithelium, so they are useful for therapy of lung cancers.

Baculovirus-mediated transfer has several advantages. Baculoviral gene transfer can occur in replicating and non-replicating cells, and can occur in renal cells, as well as in hepatocytes, neural cells, spleen, skin, and muscle. Baculovirus is non-replicating and nonpathogenic in mammalian cells. Humans lack pre-existing antibodies to recombinant baculovirus which could block infection. In addition, baculovirus is capable of incorporating and transducing very large DNA inserts.

Adeno-associated viruses (AAV) have also been employed as vectors for somatic gene therapy. AAV is a small, single-stranded (ss) DNA virus with a simple genomic organization (4–7 kb) that makes it an ideal substrate for genetic engineering. Two open reading frames encode a series of rep and cap polypeptides. Rep polypeptides (rep78, rep68, rep 62 and rep 40) are involved in replication, rescue and integration of the AAV genome. The cap proteins (VP 1, VP2 and VP3) form the virion capsid. Flanking the rep and cap open reading frames at the 5' and 3' ends are 145 bp inverted terminal repeats (ITRs), the first 125 bp of which are capable of forming Y- or T-shaped duplex structures. Of importance for the development of AAV vectors, the entire rep and cap domains can be excised and replaced with a therapeutic or reporter transgene. See B. J. Carter, in Handbook of Parvoviruses, ed., P. Tijsser, CRC Press, pp. 155–168 (1990). It has been shown that the ITRs represent the minimal sequence required for replication, rescue, packaging, and integration of the AAV genome.

Adeno-associated viruses (AAV) have significant potential in gene therapy. The viral particles are very stable and recombinant AAVs (rAAV) have "drug-like" characteristics in that rAAV can be purified by pelleting or by CsCl gradient banding. They are heat stable and can be lyophilized to a powder and rehydrated to full activity. Their DNA stably integrates into host chromosomes so expression is long-term. Their host range is broad and AAV causes no known disease so that the recombinant vectors are non-toxic.

Once introduced into a target cell, sequences of interest can be identified by conventional methods such as nucleic acid hybridization using probes comprising sequences that are homologous/complementary to the inserted gene sequences of the vector. In another approach, the sequence (s) may be identified by the presence or absence of a "marker" gene function (e.g, thymidine kinase activity, antibiotic resistance, and the like) caused by introduction of the expression vector into the target cell.

Formulations and Administration

The compounds of the invention are formulated according to standard practice, such as prepared in a carrier vehicle. The term "pharmacologically acceptable carrier" means one or more organic or inorganic ingredients, natural or synthetic, with which the mutant proto-oncogene or mutant oncoprotein is combined to facilitate its application. A suitable carrier includes sterile saline although other aqueous and non-aqueous isotonic sterile solutions and sterile suspensions known to be pharmaceutically acceptable are known to those of ordinary skill in the art. In this regard, the term "carrier" encompasses liposomes and the HIV-1 tat protein (See Chen et al., Anal. Biochem. 227: 168–175, 1995) as well as any plasmid and viral expression vectors.

Any of the novel polypeptides of this invention may be used in the form of a pharmaceutically acceptable salt. Suitable acids and bases which are capable of forming salts with the polypeptides of the present invention are well known to those of skill in the art, and include inorganic and organic acids and bases.

A compound of the invention is administered to a subject in a therapeutically-effective amount, which means an amount of the compound which produces a medically desirable result or exerts an influence on the particular condition being treated. An effective amount of a compound of the invention is capable of ameliorating or delaying progression of the diseased, degenerative or damaged condition. The effective amount can be determined on an individual basis and will be based, in part, on consideration of the physical attributes of the subject, symptoms to be treated and results sought. An effective amount can be determined by one of ordinary skill in the art employing such factors and using no more than routine experimentation.

A liposome delivery system for a compound of the invention may be any of a variety of unilamellar vesicles, multilamellar vesicles, or stable plurilamellar vesicles, and may be prepared and administered according to methods well known to those of skill in the art, for example in accordance with the teachings of U.S. Pat. Nos. 5,169,637, 4,762,915, 5,000,958 or 5,185,154. In addition, it may be desirable to express the novel polypeptides of this invention, as well as other selected polypeptides, as lipoproteins, in order to enhance their binding to liposomes. As an example, treatment of human acute renal failure with liposome-encapsulated KIM protein may be performed in vivo by introducing a KIM protein into cells in need of such treatment using liposomes. The liposomes can be delivered via catheter to the renal artery. The recombinant KIM protein is purified, for example, from CHO cells by immunoaffinity chromatography or any other convenient method, then mixed with liposomes and incorporated into them at high efficiency. The encapsulated protein may be tested in vitro for any effect on stimulating cell growth.

The compounds of the invention may be administered in any manner which is medically acceptable. This may include injections, by parenteral routes such as intravenous, intravascular, intraarterial, subcutaneous, intramuscular, intratumor, intraperitoneal, intraventricular, intraepidural, or others as well as oral, nasal, ophthalmic, rectal, or topical.

Sustained release administration is also specifically included in the invention, by such means as depot injections or erodible implants. Localized delivery is particularly contemplated, by such means as delivery via a catheter to one or more arteries, such as the renal artery or a vessel supplying a localized tumor.

EQUIVALENTS

Those skilled in the arts will recognize, or be able to ascertain using no more than routine experimentation, many equivalents to the specific embodiments of the invention described herein. All such equivalents are embraced by the following claims.

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 2566 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 615..1535

(xi) SEQUENCE DESCRIPTION: SEQ ID NO: 1:

```
GCGGCCGCGT CGACGGTGCC TGTGAGTAAA TAGATCAGGG TCTCCTTCAC AGCACATTCT        60

CCAGGAAGCC GAGCAAACAT TAGTGCTATT TTACCCAGGA GGAAATCTAG GTGTAGAGAG       120

CTCTACGGAT CTAAGGTTTG GATCTGTACC CAGTGCTTTT TTAGGTGTCT TTAGACATTT       180

CTCAGGAAGA TGTAGTCTCT GTCACCATGT GTGGCTGAAT TCTAGCTCAG TCCATCTTAT       240

TGTGTTTAAG GTAGTTGAAG TTTAGGAACC AACCAGTATG TCTCTGAGCA GAAGAGTACA       300

GTGTCCATCT TGAGGACAAG CTCATCTTTA CCATTAGAGG GCTGGCCTTG GCTTAGATTC       360

TACCGAGAAC ATACTCTCTA ATGGCTGCCC TCAGTTTTCT CTGTTTGCTG TCTTATTTGT       420

GTCATGGCCA GAAGTCATAT GGATGGCTCT ATGTGAGCAA GGACCCAGAT AGAAGAGTGT       480

ATTTGGGGGA ACAGGTTGCC CTAACAGAGA GTCCTGTGGG ATTCATGCAG TCAGGATGAA       540

GACCTGATCA GACAGAGTGT GCTGAGTGCC ACGGCTAACA AGAGTGACTT GTCACTGTCC       600

TTCAGGTCAA CACC ATG GTT CAA CTT CAA GTC TTC ATT TCA GGC CTC CTG        650
              Met Val Gln Leu Gln Val Phe Ile Ser Gly Leu Leu
                1               5                  10

CTG CTT CTT CCA GGC TCT GTA GAT TCT TAT GAA GTA GTG AAG GGG GTG        698
Leu Leu Leu Pro Gly Ser Val Asp Ser Tyr Glu Val Val Lys Gly Val
         15                  20                  25

GTG GGT CAC CCT GTC ACA ATT CCA TGT ACT TAC TCA ACA CGT GGA GGA        746
Val Gly His Pro Val Thr Ile Pro Cys Thr Tyr Ser Thr Arg Gly Gly
     30                  35                  40

ATC ACA ACG ACA TGT TGG GGC CGG GGG CAA TGC CCA TAT TCT AGT TGT        794
Ile Thr Thr Thr Cys Trp Gly Arg Gly Gln Cys Pro Tyr Ser Ser Cys
 45                  50                  55                  60

CAA AAT ATA CTT ATT TGG ACC AAT GGA TAC CAA GTC ACC TAT CGG AGC        842
Gln Asn Ile Leu Ile Trp Thr Asn Gly Tyr Gln Val Thr Tyr Arg Ser
                 65                  70                  75

AGC GGT CGA TAC AAC ATA AAG GGG CGT ATT TCA GAA GGA GAC GTA TCC        890
Ser Gly Arg Tyr Asn Ile Lys Gly Arg Ile Ser Glu Gly Asp Val Ser
             80                  85                  90

TTG ACA ATA GAG AAC TCT GTT GAT AGT GAT AGT GGT CTG TAT TGT TGC        938
Leu Thr Ile Glu Asn Ser Val Asp Ser Asp Ser Gly Leu Tyr Cys Cys
```

-continued

```
              95                  100                       105
CGA GTG GAG ATT CCT GGA TGG TTC AAC GAT CAG AAA ATG ACC TTT TCA      986
Arg Val Glu Ile Pro Gly Trp Phe Asn Asp Gln Lys Met Thr Phe Ser
        110                 115                 120

TTG GAA GTT AAA CCA GAA ATT CCC ACA AGT CCT CCA ACA AGA CCC ACA     1034
Leu Glu Val Lys Pro Glu Ile Pro Thr Ser Pro Pro Thr Arg Pro Thr
125                 130                 135                 140

ACT ACA AGA CCC ACA ACC ACA AGG CCC ACA ACT ATT TCA ACA AGA TCC     1082
Thr Thr Arg Pro Thr Thr Thr Arg Pro Thr Thr Ile Ser Thr Arg Ser
                145                 150                 155

ACA CAT GTA CCA ACA TCA ACC AGA GTC TCC ACC TCT ACT CCA ACA CCA     1130
Thr His Val Pro Thr Ser Thr Arg Val Ser Thr Ser Thr Pro Thr Pro
            160                 165                 170

GAA CAA ACA CAG ACT CAC AAA CCA GAA ATC ACT ACA TTT TAT GCC CAT     1178
Glu Gln Thr Gln Thr His Lys Pro Glu Ile Thr Thr Phe Tyr Ala His
        175                 180                 185

GAG ACA ACT GCT GAG GTG ACA GAA ACT CCA TCA TAT ACT CCT GCA GAC     1226
Glu Thr Thr Ala Glu Val Thr Glu Thr Pro Ser Tyr Thr Pro Ala Asp
190                 195                 200

TGG AAT GGC ACT GTG ACA TCC TCA GAG GAG GCC TGG AAT AAT CAC ACT     1274
Trp Asn Gly Thr Val Thr Ser Ser Glu Glu Ala Trp Asn Asn His Thr
205                 210                 215                 220

GTA AGA ATC CCT TTG AGG AAG CCG CAG AGA AAC CCG ACT AAG GGC TTC     1322
Val Arg Ile Pro Leu Arg Lys Pro Gln Arg Asn Pro Thr Lys Gly Phe
                225                 230                 235

TAT GTT GGC ATG TCC GTT GCA GCC CTG CTG CTG CTG CTG CTT GCG AGC     1370
Tyr Val Gly Met Ser Val Ala Ala Leu Leu Leu Leu Leu Leu Ala Ser
            240                 245                 250

ACC GTG GTT GTC ACC AGG TAC ATC ATT ATA AGA AAG AAG ATG GGC TCT     1418
Thr Val Val Val Thr Arg Tyr Ile Ile Ile Arg Lys Lys Met Gly Ser
        255                 260                 265

CTG AGC TTT GTT GCC TTC CAT GTC TCT AAG AGT AGA GCT TTG CAG AAC     1466
Leu Ser Phe Val Ala Phe His Val Ser Lys Ser Arg Ala Leu Gln Asn
270                 275                 280

GCA GCG ATT GTG CAT CCC CGA GCT GAA GAC AAC ATC TAC ATT ATT GAA     1514
Ala Ala Ile Val His Pro Arg Ala Glu Asp Asn Ile Tyr Ile Ile Glu
285                 290                 295                 300

GAT AGA TCT CGA GGT GCA GAA TGAGTCCCAG AGGCCTTCTG TGGGGCCTTC        1565
Asp Arg Ser Arg Gly Ala Glu
                305

TGCCTGGGAT TACAGAGATC GTGACTGATT TCACAGAGTA AAATACCCAT TCCAGCTCCT   1625

GGGAGATTTT GTGTTTTGGT TCTTCCAGCT GCAGTGGAGA GGGTAACCCT CTACCCTGTA   1685

TATGCAAAAC TCGAGGTTAA CATCATCCTA ATTCTTGTAT CAGCAACACC TCAGTGTCTC   1745

CACTCACTGC AGCGATTCTC TCAAATGTGA ACATTTTAGA AGTTTGTGTT TCCTTTTGTC   1805

CATGTAATCA TTGGTAATAC AAGAATTTTA TCTTGTTTAT TAAAACCATT AATGAGAGGG   1865

GAATAGGAAT TAAAAGCTGG TGGGAAGGGC CTCCTGAATT TAGAAGCACT TCATGATTGT   1925

GTTTATCTCT TTTATTGTAA TTTGAAATGT TACTTCTATC CTTCCAAGG GGCAAAATCA   1985

TGGGAGCATG GAGGTTTTAA TTGCCCTCAT AGATAAGTAG AAGAAGAGAG TCTAATGCCA   2045

CCAATAGAGG TGGTTATGCT TTCTCACAGC TCTGGAAATA TGATCATTTA TTATGCAGTT   2105

GATCTTAGGA TGAGGATGGG TTTCTTAGGA GGAGAGGTTA CCATGGTGAG TGGACCAGGC   2165

ACACATCAGG GGAAGAAAAC AATGGATCAA GGGATTGAGT TCATTAGAGC CATTTCCACT   2225

CCACTTCTGT CTTGATGCTC AGTGTTCCTA AACTCACCCA CTGAGCTCTG AATTAGGTGC   2285

AGGGAGGAGA CGTGCAGAAA CGAAAGAGGA AAGAAAGGAG AGAGAGCAGG ACACAGGCTT   2345
```

-continued

```
TCTGCTGAGA AGAGTCCTAT TGCAGGTGTG ACAGTGTTTG GGACTACCAC GGGTTTCCTT    2405

CAGACTTCTA AGTTTCTAAA TCACTATCAT GTGATCATAT TTATTTTTAA AATTATTTCA    2465

GAAAGACACC ACATTTTCAA TAATAAATCA GTTTGTCACA ATTAATAAAA TATTTTGTTT    2525

GCTAAGAAGT AAAAAAAAAA AAAAAAGTC GACGCGGCCG C                        2566
```

(2) INFORMATION FOR SEQ ID NO: 2:

(i) SEQUENCE CHARACTERISTICS:
     (A) LENGTH: 2084 base pairs
     (B) TYPE: nucleic acid
     (C) STRANDEDNESS: single
     (D) TOPOLOGY: linear (ii) MOLECULE TYPE: cDNA (ix) FEATURE:
     (A) NAME/KEY: CDS
     (B) LOCATION: 145..1065

(xi) SEQUENCE DESCRIPTION: SEQ ID NO: 2:

```
GCGGCCGCGT CGACGGTGCC TGTGAGTAAA TAGATCAGGG TCTCCTTCAC AGCACATTCT      60

CCAGGAAGCC GAGCAAACAT TAGTGCTATT TTACCCAGGA GGAAATCTAG GTGTAGAGAG     120

CTCTACGGAT CTAAGGTCAA CACC ATG GTT CAA CTT CAA GTC TTC ATT TCA        171
                          Met Val Gln Leu Gln Val Phe Ile Ser
                           1               5

GGC CTC CTG CTG CTT CTT CCA GGC TCT GTA GAT TCT TAT GAA GTA GTG       219
Gly Leu Leu Leu Leu Leu Pro Gly Ser Val Asp Ser Tyr Glu Val Val
 10                  15                  20                  25

AAG GGG GTG GTG GGT CAC CCT GTC ACA ATT CCA TGT ACT TAC TCA ACA       267
Lys Gly Val Val Gly His Pro Val Thr Ile Pro Cys Thr Tyr Ser Thr
             30                  35                  40

CGT GGA GGA ATC ACA ACG ACA TGT TGG GGC CGG GGG CAA TGC CCA TAT       315
Arg Gly Gly Ile Thr Thr Thr Cys Trp Gly Arg Gly Gln Cys Pro Tyr
         45                  50                  55

TCT AGT TGT CAA AAT ATA CTT ATT TGG ACC AAT GGA TAC CAA GTC ACC       363
Ser Ser Cys Gln Asn Ile Leu Ile Trp Thr Asn Gly Tyr Gln Val Thr
     60                  65                  70

TAT CGG AGC AGC GGT CGA TAC AAC ATA AAG GGG CGT ATT TCA GAA GGA       411
Tyr Arg Ser Ser Gly Arg Tyr Asn Ile Lys Gly Arg Ile Ser Glu Gly
 75                  80                  85

GAC GTA TCC TTG ACA ATA GAG AAC TCT GTT GAT AGT GAT AGT GGT CTG       459
Asp Val Ser Leu Thr Ile Glu Asn Ser Val Asp Ser Asp Ser Gly Leu
 90                  95                 100                 105

TAT TGT TGC CGA GTG GAG ATT CCT GGA TGG TTC AAC GAT CAG AAA ATG       507
Tyr Cys Cys Arg Val Glu Ile Pro Gly Trp Phe Asn Asp Gln Lys Met
             110                 115                 120

ACC TTT TCA TTG GAA GTT AAA CCA GAA ATT CCC ACA AGT CCT CCA ACA       555
Thr Phe Ser Leu Glu Val Lys Pro Glu Ile Pro Thr Ser Pro Pro Thr
         125                 130                 135

AGA CCC ACA ACT ACA AGA CCC ACA ACC ACA AGG CCC ACA ACT ATT TCA       603
Arg Pro Thr Thr Thr Arg Pro Thr Thr Thr Arg Pro Thr Thr Ile Ser
     140                 145                 150

ACA AGA TCC ACA CAT GTA CCA ACA TCA ACC AGA GTC TCC ACC TCT ACT       651
Thr Arg Ser Thr His Val Pro Thr Ser Thr Arg Val Ser Thr Ser Thr
 155                 160                 165

CCA ACA CCA GAA CAA ACA CAG ACT CAC AAA CCA GAA ATC ACT ACA TTT       699
Pro Thr Pro Glu Gln Thr Gln Thr His Lys Pro Glu Ile Thr Thr Phe
170                 175                 180                 185

TAT GCC CAT GAG ACA ACT GCT GAG GTG ACA GAA ACT CCA TCA TAT ACT       747
```

```
Tyr Ala His Glu Thr Thr Ala Glu Val Thr Glu Thr Pro Ser Tyr Thr
            190                 195                 200

CCT GCA GAC TGG AAT GGC ACT GTG ACA TCC TCA GAG GAG GCC TGG AAT       795
Pro Ala Asp Trp Asn Gly Thr Val Thr Ser Ser Glu Glu Ala Trp Asn
            205                 210                 215

AAT CAC ACT GTA AGA ATC CCT TTG AGG AAG CCG CAG AGA AAC CCG ACT       843
Asn His Thr Val Arg Ile Pro Leu Arg Lys Pro Gln Arg Asn Pro Thr
            220                 225                 230

AAG GGC TTC TAT GTT GGC ATG TCC GTT GCA GCC CTG CTG CTG CTG CTG       891
Lys Gly Phe Tyr Val Gly Met Ser Val Ala Ala Leu Leu Leu Leu Leu
            235                 240                 245

CTT GCG AGC ACC GTG GTT GTC ACC AGG TAC ATC ATT ATA AGA AAG AAG       939
Leu Ala Ser Thr Val Val Val Thr Arg Tyr Ile Ile Ile Arg Lys Lys
250                 255                 260                 265

ATG GGC TCT CTG AGC TTT GTT GCC TTC CAT GTC TCT AAG AGT AGA GCT       987
Met Gly Ser Leu Ser Phe Val Ala Phe His Val Ser Lys Ser Arg Ala
            270                 275                 280

TTG CAG AAC GCA GCG ATT GTG CAT CCC CGA GCT GAA GAC AAC ATC TAC      1035
Leu Gln Asn Ala Ala Ile Val His Pro Arg Ala Glu Asp Asn Ile Tyr
            285                 290                 295

ATT ATT GAA GAT AGA TCT CGA GGT GCA GAA TGAGTCCCAG AGGCCTTCTG        1085
Ile Ile Glu Asp Arg Ser Arg Gly Ala Glu
            300                 305

TGGGGCCTTC TGCCTGGGAT TACAGAGATC GTGACTGATT TCACAGAGTA AAATACCC1145

TCCAGCTCCT GGGAGATTTT GTGTTTTGGT TCTTCCAGCT GCAGTGGAGA GGGTAACC1205

CTACCCTGTA TATGCAAAAC TCGAGGTTAA CATCATCCTA ATTCTTGTAT CAGCAACA1265

TCAGTGTCTC CACTCACTGC AGCGATTCTC TCAAATGTGA ACATTTTAGA AGTTTGTG1325

TCCTTTTGTC CATGTAATCA TTGGTAATAC AAGAATTTTA TCTTGTTTAT TAAAACCA1385

AATGAGAGGG GAATAGGAAT TAAAAGCTGG TGGGAAGGGC CTCCTGAATT TAGAAGCA1445

TCATGATTGT GTTTATCTCT TTTATTGTAA TTTGAAATGT TACTTCTATC CTTCCCAA1505

GGCAAAATCA TGGGAGCATG GAGGTTTTAA TTGCCCTCAT AGATAAGTAG AAGAAGAG1565

TCTAATGCCA CCAATAGAGG TGGTTATGCT TTCTCACAGC TCTGGAAATA TGATCATT1625

TTATGCAGTT GATCTTAGGA TGAGGATGGG TTTCTTAGGA GGAGAGGTTA CCATGGTG1685

TGGACCAGGC ACACATCAGG GGAAGAAAAC AATGGATCAA GGGATTGAGT TCATTAGA1745

CATTTCCACT CCACTTCTGT CTTGATGCTC AGTGTTCCTA AACTCACCCA CTGAGCTC1805

AATTAGGTGC AGGGAGGAGA CGTGCAGAAA CGAAAGAGGA AGAAAGGAG AGAGAGCA1865

ACACAGGCTT TCTGCTGAGA GAAGTCCTAT TGCAGGTGTG ACAGTGTTTG GGACTACC1925

GGGTTTCCTT CAGACTTCTA AGTTTCTAAA TCACTATCAT GTGATCATAT TTATTTTT1985

AATTATTTCA GAAAGACACC ACATTTTCAA TAATAAATCA GTTTGTCACA ATTAATAA2045

TATTTTGTTT GCTAAGAAGT AAAAAGTCGA CGCGGCCGC                         2084

(2) INFORMATION FOR SEQ ID NO: 3:

(i) SEQUENCE CHARACTERISTICS:
        (A) LENGTH: 307 amino acids
        (B) TYPE: amino acid
        (D) TOPOLOGY: linear (ii) MOLECULE TYPE: protein (xi) SEQUENCE DESCRIPTION: SEQ ID NO: 3:

Met Val Gln Leu Gln Val Phe Ile Ser Gly Leu Leu Leu Leu Leu Pro
1               5                   10                  15
```

```
Gly Ser Val Asp Ser Tyr Glu Val Val Lys Gly Val Val Gly His Pro
            20                  25                  30

Val Thr Ile Pro Cys Thr Tyr Ser Thr Arg Gly Ile Thr Thr Thr
        35                  40                  45

Cys Trp Gly Arg Gly Gln Cys Pro Tyr Ser Ser Cys Gln Asn Ile Leu
    50                  55                  60

Ile Trp Thr Asn Gly Tyr Gln Val Thr Tyr Arg Ser Ser Gly Arg Tyr
65                  70                  75                  80

Asn Ile Lys Gly Arg Ile Ser Glu Gly Asp Val Ser Leu Thr Ile Glu
                85                  90                  95

Asn Ser Val Asp Ser Asp Ser Gly Leu Tyr Cys Cys Arg Val Glu Ile
                100                 105                 110

Pro Gly Trp Phe Asn Asp Gln Lys Met Thr Phe Ser Leu Glu Val Lys
        115                 120                 125

Pro Glu Ile Pro Thr Ser Pro Pro Thr Arg Pro Thr Thr Thr Arg Pro
    130                 135                 140

Thr Thr Thr Arg Pro Thr Thr Ile Ser Thr Arg Ser Thr His Val Pro
145                 150                 155                 160

Thr Ser Thr Arg Val Ser Thr Ser Thr Pro Thr Pro Glu Gln Thr Gln
                165                 170                 175

Thr His Lys Pro Glu Ile Thr Thr Phe Tyr Ala His Glu Thr Thr Ala
                180                 185                 190

Glu Val Thr Glu Thr Pro Ser Tyr Thr Pro Ala Asp Trp Asn Gly Thr
        195                 200                 205

Val Thr Ser Ser Glu Glu Ala Trp Asn Asn His Thr Val Arg Ile Pro
210                 215                 220

Leu Arg Lys Pro Gln Arg Asn Pro Thr Lys Gly Phe Tyr Val Gly Met
225                 230                 235                 240

Ser Val Ala Ala Leu Leu Leu Leu Leu Ala Ser Thr Val Val Val
                245                 250                 255

Thr Arg Tyr Ile Ile Ile Arg Lys Lys Met Gly Ser Leu Ser Phe Val
            260                 265                 270

Ala Phe His Val Ser Lys Ser Arg Ala Leu Gln Asn Ala Ala Ile Val
        275                 280                 285

His Pro Arg Ala Glu Asp Asn Ile Tyr Ile Ile Glu Asp Arg Ser Arg
    290                 295                 300

Gly Ala Glu
305

(2) INFORMATION FOR SEQ ID NO: 4:

(i) SEQUENCE CHARACTERISTICS:
        (A) LENGTH: 2303 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 107..1822

(xi) SEQUENCE DESCRIPTION: SEQ ID NO: 4:

GCGGCCGCGT CGACTCGCAG GAGGCCGGCA CTCTGACTCC TGGTGGATGG GACTAGGGAG      60

TCAGAGTCAA GCCCTGACTG GCTGAGGGCG GGCGCTCCGA GTCAGC ATG GAA AGT      115
                                                Met Glu Ser
```

```
                                                     1
CTC TGC GGG GTC CTG GTA TTT CTG CTG CTG GCT GCA GGA CTG CCG CTC       163
Leu Cys Gly Val Leu Val Phe Leu Leu Leu Ala Ala Gly Leu Pro Leu
         5                  10                  15

CAG GCG GCC AAG CGG TTC CGT GAT GTG CTG GGC CAT GAG CAG TAT CCG       211
Gln Ala Ala Lys Arg Phe Arg Asp Val Leu Gly His Glu Gln Tyr Pro
 20                  25                  30                  35

GAT CAC ATG AGG GAG AAC AAC CAA TTA CGT GGC TGG TCT TCA GAT GAA       259
Asp His Met Arg Glu Asn Asn Gln Leu Arg Gly Trp Ser Ser Asp Glu
                 40                  45                  50

AAT GAA TGG GAT GAA CAG CTG TAT CCA GTG TGG AGG AGG GGA GAG GGC       307
Asn Glu Trp Asp Glu Gln Leu Tyr Pro Val Trp Arg Arg Gly Glu Gly
             55                  60                  65

AGA TGG AAG GAC TCC TGG GAA GGA GGC CGT GTG CAG GCA GCC CTA ACC       355
Arg Trp Lys Asp Ser Trp Glu Gly Gly Arg Val Gln Ala Ala Leu Thr
         70                  75                  80

AGT GAT TCA CCG GCC TTG GTG GGT TCC AAT ATC ACC TTC GTA GTG AAC       403
Ser Asp Ser Pro Ala Leu Val Gly Ser Asn Ile Thr Phe Val Val Asn
 85                  90                  95

CTG GTG TTC CCC AGA TGC CAG AAG GAA GAT GCC AAC GGC AAT ATC GTC       451
Leu Val Phe Pro Arg Cys Gln Lys Glu Asp Ala Asn Gly Asn Ile Val
100                 105                 110                 115

TAT GAG AGG AAC TGC AGA AGT GAT TTG GAG CTG GCT TCT GAC CCG TAT       499
Tyr Glu Arg Asn Cys Arg Ser Asp Leu Glu Leu Ala Ser Asp Pro Tyr
                120                 125                 130

GTC TAC AAC TGG ACC ACA GGG GCA GAC GAT GAG GAC TGG GAA GAC AGC       547
Val Tyr Asn Trp Thr Thr Gly Ala Asp Asp Glu Asp Trp Glu Asp Ser
            135                 140                 145

ACC AGC CAA GGC CAG CAC CTC AGG TTC CCC GAC GGG AAG CCC TTC CCT       595
Thr Ser Gln Gly Gln His Leu Arg Phe Pro Asp Gly Lys Pro Phe Pro
        150                 155                 160

CGC CCC CAC GGA CGG AAG AAA TGG AAC TTC GTC TAC GTC TTC CAC ACA       643
Arg Pro His Gly Arg Lys Lys Trp Asn Phe Val Tyr Val Phe His Thr
165                 170                 175

CTT GGT CAG TAT TTT CAA AAG CTG GGT CGG TGT TCA GCA CGA GTT TCT       691
Leu Gly Gln Tyr Phe Gln Lys Leu Gly Arg Cys Ser Ala Arg Val Ser
180                 185                 190                 195

ATA AAC ACA GTC AAC TTG ACA GTT GGC CCT CAG GTC ATG GAA GTG ATT       739
Ile Asn Thr Val Asn Leu Thr Val Gly Pro Gln Val Met Glu Val Ile
                200                 205                 210

GTC TTT CGA AGA CAC GGC CGG GCA TAC ATT CCC ATC TCC AAA GTG AAA       787
Val Phe Arg Arg His Gly Arg Ala Tyr Ile Pro Ile Ser Lys Val Lys
            215                 220                 225

GAC GTG TAT GTG ATA ACA GAT CAG ATC CCT ATA TTC GTG ACC ATG TAC       835
Asp Val Tyr Val Ile Thr Asp Gln Ile Pro Ile Phe Val Thr Met Tyr
        230                 235                 240

CAG AAG AAT GAC CGG AAC TCG TCT GAT GAA ACC TTC CTC AGA GAC CTC       883
Gln Lys Asn Asp Arg Asn Ser Ser Asp Glu Thr Phe Leu Arg Asp Leu
245                 250                 255

CCC ATT TTC TTC GAT GTC CTC ATT CAC GAT CCC AGT CAT TTC CTC AAC       931
Pro Ile Phe Phe Asp Val Leu Ile His Asp Pro Ser His Phe Leu Asn
260                 265                 270                 275

TAC TCT GCC ATT TCC TAC AAG TGG AAC TTT GGG GAC AAC ACT GGC CTG       979
Tyr Ser Ala Ile Ser Tyr Lys Trp Asn Phe Gly Asp Asn Thr Gly Leu
                280                 285                 290

TTT GTC TCC AAC AAT CAC ACT TTG AAT CAC ACG TAT GTG CTC AAT GGA      1027
Phe Val Ser Asn Asn His Thr Leu Asn His Thr Tyr Val Leu Asn Gly
            295                 300                 305

ACC TTC AAC TTT AAC CTC ACC GTG CAA ACT GCA GTG CCG GGA CCA TGC      1075
```

```
                                                         -continued

Thr Phe Asn Phe Asn Leu Thr Val Gln Thr Ala Val Pro Gly Pro Cys
                310                 315                 320
CCC TCA CCC ACA CCT TCG CCT TCT TCT TCG ACT TCT CCT TCG CCT GCA          1123
Pro Ser Pro Thr Pro Ser Pro Ser Ser Ser Thr Ser Pro Ser Pro Ala
325                 330                 335
TCT TCG CCT TCA CCC ACA TTA TCA ACA CCT AGT CCC TCT TTA ATG CCT          1171
Ser Ser Pro Ser Pro Thr Leu Ser Thr Pro Ser Pro Ser Leu Met Pro
340                 345                 350                 355
ACT GGC CAC AAA TCC ATG GAG CTG AGT GAC ATT TCC AAT GAA AAC TGC          1219
Thr Gly His Lys Ser Met Glu Leu Ser Asp Ile Ser Asn Glu Asn Cys
                360                 365                 370
CGA ATA AAC AGA TAT GGT TAC TTC AGA GCC ACC ATC ACA ATT GTA GAT          1267
Arg Ile Asn Arg Tyr Gly Tyr Phe Arg Ala Thr Ile Thr Ile Val Asp
                375                 380                 385
GGA ATC CTA GAA GTC AAC ATC ATC CAG GTA GCA GAT GTC CCA ATC CCC          1315
Gly Ile Leu Glu Val Asn Ile Ile Gln Val Ala Asp Val Pro Ile Pro
                390                 395                 400
ACA CCG CAG CCT GAC AAC TCA CTG ATG GAC TTC ATT GTG ACC TGC AAA          1363
Thr Pro Gln Pro Asp Asn Ser Leu Met Asp Phe Ile Val Thr Cys Lys
405                 410                 415
GGG GCC ACT CCC ACG GAA GCC TGT ACG ATC ATC TCT GAC CCC ACC TGC          1411
Gly Ala Thr Pro Thr Glu Ala Cys Thr Ile Ile Ser Asp Pro Thr Cys
420                 425                 430                 435
CAG ATC GCC CAG AAC AGG GTG TGC AGC CCG GTG GCT GTG GAT GAG CTG          1459
Gln Ile Ala Gln Asn Arg Val Cys Ser Pro Val Ala Val Asp Glu Leu
                440                 445                 450
TGC CTC CTG TCC GTG AGG AGA GCC TTC AAT GGG TCC GGC ACG TAC TGT          1507
Cys Leu Leu Ser Val Arg Arg Ala Phe Asn Gly Ser Gly Thr Tyr Cys
                455                 460                 465
GTG AAT TTC ACT CTG GGA GAC GAT GCA AGC CTG GCC CTC ACC AGC GCC          1555
Val Asn Phe Thr Leu Gly Asp Asp Ala Ser Leu Ala Leu Thr Ser Ala
                470                 475                 480
CTG ATC TCT ATC CCT GGC AAA GAC CTA GGC TCC CCT CTG AGA ACA GTG          1603
Leu Ile Ser Ile Pro Gly Lys Asp Leu Gly Ser Pro Leu Arg Thr Val
485                 490                 495
AAT GGT GTC CTG ATC TCC ATT GGC TGC CTG GCC ATG TTT GTC ACC ATG          1651
Asn Gly Val Leu Ile Ser Ile Gly Cys Leu Ala Met Phe Val Thr Met
500                 505                 510                 515
GTT ACC ATC TTG CTG TAC AAA AAA CAC AAG ACG TAC AAG CCA ATA GGA          1699
Val Thr Ile Leu Leu Tyr Lys Lys His Lys Thr Tyr Lys Pro Ile Gly
                520                 525                 530
AAC TGC ACC AGG AAC GTG GTC AAG GGC AAA GGC TGA GTT GTT TTT CTC          1747
Asn Cys Thr Arg Asn Val Val Lys Gly Lys Gly Leu Ser Val Phe Leu
                535                 540                 545
AGC CAT GCA AAA GCC CCG TTC TCC CGA GGA GAC CGG GAG AAG GAT CCA          1795
Ser His Ala Lys Ala Pro Phe Ser Arg Gly Asp Arg Glu Lys Asp Pro
                550                 555                 560
CTG CTC CAG GAC AAG CCA TGG ATG CTC TAAGTCTTCA CTCTCACTTC                1842
Leu Leu Gln Asp Lys Pro Trp Met Leu
565                 570
TGACTGGGAA CCCACTCTTC TGTGCATGTA TGTGAGCTGT GCAGAAGTAC ATGACTGGTA        1902
GCTGTTGTTT TCTACGGATT ATTGTAAAAT GTATATCATG GTTTAGGGAG CGTAGTTAAT        1962
TGGCATTTTA GTGAAGGGAT GGGAAGACAG TATTTCTTCA CATCTGTATT GTGGTTTTTA        2022
TACTGTTAAT AGGGTGGGCA CATTGTGTCT GAAGGGGGAG GGGGAGGTCA CTGCTACTTA        2082
AGGTCCTAGG TTAACTGGGA GAGGATGCCC CAGGCTCCTT AGATTTCTAC ACAAGATGTG        2142
CCTGAACCCA GCTAGTCCTG ACCTAAAGGC CATGCTTCAT CAACTCTATC TCAGCTCATT        2202
```

```
GAACATACCT GAGCACCTGA TGGAATTATA ATGGAACCAA GCTTGTTGTA TGGTGTGTGT    2262

GTGTACATAA GATACTCATT AAAAAGACAG TCTATTAAAA A                       2303
```

(2) INFORMATION FOR SEQ ID NO: 5:

(i) SEQUENCE CHARACTERISTICS:
        (A) LENGTH: 572 amino acids
        (B) TYPE: amino acid
        (D) TOPOLOGY: linear (ii) MOLECULE TYPE: protein (xi) SEQUENCE DESCRIPTION: SEQ ID NO: 5:

```
Met Glu Ser Leu Cys Gly Val Leu Val Phe Leu Leu Leu Ala Ala Gly
  1               5                  10                  15

Leu Pro Leu Gln Ala Ala Lys Arg Phe Arg Asp Val Leu Gly His Glu
             20                  25                  30

Gln Tyr Pro Asp His Met Arg Glu Asn Asn Gln Leu Arg Gly Trp Ser
         35                  40                  45

Ser Asp Glu Asn Glu Trp Asp Glu Gln Leu Tyr Pro Val Trp Arg Arg
 50                  55                  60

Gly Glu Gly Arg Trp Lys Asp Ser Trp Glu Gly Gly Arg Val Gln Ala
 65                  70                  75                  80

Ala Leu Thr Ser Asp Ser Pro Ala Leu Val Gly Ser Asn Ile Thr Phe
             85                  90                  95

Val Val Asn Leu Val Phe Pro Arg Cys Gln Lys Glu Asp Ala Asn Gly
            100                 105                 110

Asn Ile Val Tyr Glu Arg Asn Cys Arg Ser Asp Leu Glu Leu Ala Ser
            115                 120                 125

Asp Pro Tyr Val Tyr Asn Trp Thr Thr Gly Ala Asp Asp Glu Asp Trp
        130                 135                 140

Glu Asp Ser Thr Ser Gln Gly Gln His Leu Arg Phe Pro Asp Gly Lys
145                 150                 155                 160

Pro Phe Pro Arg Pro His Gly Arg Lys Lys Trp Asn Phe Val Tyr Val
                165                 170                 175

Phe His Thr Leu Gly Gln Tyr Phe Gln Lys Leu Gly Arg Cys Ser Ala
            180                 185                 190

Arg Val Ser Ile Asn Thr Val Asn Leu Thr Val Gly Pro Gln Val Met
        195                 200                 205

Glu Val Ile Val Phe Arg Arg His Gly Arg Ala Tyr Ile Pro Ile Ser
    210                 215                 220

Lys Val Lys Asp Val Tyr Val Ile Thr Asp Gln Ile Pro Ile Phe Val
225                 230                 235                 240

Thr Met Tyr Gln Lys Asn Asp Arg Asn Ser Ser Asp Glu Thr Phe Leu
                245                 250                 255

Arg Asp Leu Pro Ile Phe Phe Asp Val Leu Ile His Asp Pro Ser His
            260                 265                 270

Phe Leu Asn Tyr Ser Ala Ile Ser Tyr Lys Trp Asn Phe Gly Asp Asn
        275                 280                 285

Thr Gly Leu Phe Val Ser Asn Asn His Thr Leu Asn His Thr Tyr Val
    290                 295                 300

Leu Asn Gly Thr Phe Asn Phe Asn Leu Thr Val Gln Thr Ala Val Pro
305                 310                 315                 320

Gly Pro Cys Pro Ser Pro Thr Pro Ser Pro Ser Ser Thr Ser Pro
                325                 330                 335
```

```
Ser Pro Ala Ser Ser Pro Ser Pro Thr Leu Ser Thr Pro Ser Pro Ser
            340                 345                 350

Leu Met Pro Thr Gly His Lys Ser Met Glu Leu Ser Asp Ile Ser Asn
            355                 360                 365

Glu Asn Cys Arg Ile Asn Arg Tyr Gly Tyr Phe Arg Ala Thr Ile Thr
370                 375                 380

Ile Val Asp Gly Ile Leu Glu Val Asn Ile Ile Gln Val Ala Asp Val
385                 390                 395                 400

Pro Ile Pro Thr Pro Gln Pro Asp Asn Ser Leu Met Asp Phe Ile Val
            405                 410                 415

Thr Cys Lys Gly Ala Thr Pro Thr Glu Ala Cys Thr Ile Ile Ser Asp
            420                 425                 430

Pro Thr Cys Gln Ile Ala Gln Asn Arg Val Cys Ser Pro Val Ala Val
            435                 440                 445

Asp Glu Leu Cys Leu Leu Ser Val Arg Arg Ala Phe Asn Gly Ser Gly
450                 455                 460

Thr Tyr Cys Val Asn Phe Thr Leu Gly Asp Asp Ala Ser Leu Ala Leu
465                 470                 475                 480

Thr Ser Ala Leu Ile Ser Ile Pro Gly Lys Asp Leu Gly Ser Pro Leu
            485                 490                 495

Arg Thr Val Asn Gly Val Leu Ile Ser Ile Gly Cys Leu Ala Met Phe
            500                 505                 510

Val Thr Met Val Thr Ile Leu Leu Tyr Lys Lys His Lys Thr Tyr Lys
            515                 520                 525

Pro Ile Gly Asn Cys Thr Arg Asn Val Val Lys Gly Lys Gly Leu Ser
            530                 535                 540

Val Phe Leu Ser His Ala Lys Ala Pro Phe Ser Arg Gly Asp Arg Glu
545                 550                 555                 560

Lys Asp Pro Leu Leu Gln Asp Lys Pro Trp Met Leu
            565                 570

(2) INFORMATION FOR SEQ ID NO: 6:

(i) SEQUENCE CHARACTERISTICS:
        (A) LENGTH: 1795 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 278..1279

(xi) SEQUENCE DESCRIPTION: SEQ ID NO: 6:

GCGGCCGCGT CGACGAAGCT GGGAAGTCAG GGGCTGTTTC TGTGGGCAGC TTTCCCTGTC      60

CTTTGGAAGG CACAGAGCTC TCAGCTGCAG GGAACTAACA GAGCTCTGAA GCCGTTATAT     120

GTGGTCTTCT CTCATTTCCA GCAGAGCAGG CTCATATGAA TCAACCAACT GGGTGAAAAG     180

ATAAGTTGCA ATCTGAGATT TAAGACTTGA TCAGATACCA TCTGGTGGAG GGTACCAACC     240

AGCCTGTCTG CTCATTTTCC TTCAGGCTGA TCCCATA ATG CAT CCT CAA GTG GTC     295
                                        Met His Pro Gln Val Val
                                         1               5

ATC TTA AGC CTC ATC CTA CAT CTG GCA GAT TCT GTA GCT GGT TCT GTA      343
Ile Leu Ser Leu Ile Leu His Leu Ala Asp Ser Val Ala Gly Ser Val
        10                  15                  20

AAG GTT GGT GGA GAG GCA GGT CCA TCT GTC ACA CTA CCC TGC CAC TAC      391
```

-continued

```
               Lys Val Gly Gly Glu Ala Gly Pro Ser Val Thr Leu Pro Cys His Tyr
                    25                  30                  35

AGT GGA GCT GTC ACA TCA ATG TGC TGG AAT AGA GGC TCA TGT TCT CTA            439
Ser Gly Ala Val Thr Ser Met Cys Trp Asn Arg Gly Ser Cys Ser Leu
         40                  45                  50

TTC ACA TGC CAA AAT GGC ATT GTC TGG ACC AAT GGA ACC CAC GTC ACC            487
Phe Thr Cys Gln Asn Gly Ile Val Trp Thr Asn Gly Thr His Val Thr
 55                  60                  65                  70

TAT CGG AAG GAC ACA CGC TAT AAG CTA TTG GGG GAC CTT TCA AGA AGG            535
Tyr Arg Lys Asp Thr Arg Tyr Lys Leu Leu Gly Asp Leu Ser Arg Arg
                 75                  80                  85

GAT GTC TCT TTG ACC ATA GAA AAT ACA GCT GTG TCT GAC AGT GGC GTA            583
Asp Val Ser Leu Thr Ile Glu Asn Thr Ala Val Ser Asp Ser Gly Val
             90                  95                 100

TAT TGT TGC CGT GTT GAG CAC CGT GGG TGG TTC AAT GAC ATG AAA ATC            631
Tyr Cys Cys Arg Val Glu His Arg Gly Trp Phe Asn Asp Met Lys Ile
        105                 110                 115

ACC GTA TCA TTG GAG ATT GTG CCA CCC AAG GTC ACG ACT ACT CCA ATT            679
Thr Val Ser Leu Glu Ile Val Pro Pro Lys Val Thr Thr Thr Pro Ile
    120                 125                 130

GTC ACA ACT GTT CCA ACC GTC ACG ACT GTT CGA ACG AGC ACC ACT GTT            727
Val Thr Thr Val Pro Thr Val Thr Thr Val Arg Thr Ser Thr Thr Val
135                 140                 145                 150

CCA ACG ACA ACG ACT GTT CCA ACG ACA ACT GTT CCA ACA ACA ATG AGC            775
Pro Thr Thr Thr Thr Val Pro Thr Thr Thr Val Pro Thr Thr Met Ser
                155                 160                 165

ATT CCA ACG ACA ACG ACT GTT CCG ACG ACA ATG ACT GTT TCA ACG ACA            823
Ile Pro Thr Thr Thr Thr Val Pro Thr Thr Met Thr Val Ser Thr Thr
            170                 175                 180

ACG AGC GTT CCA ACG ACA ACG AGC ATT CCA ACA ACA ACA AGT GTT CCA            871
Thr Ser Val Pro Thr Thr Thr Ser Ile Pro Thr Thr Thr Ser Val Pro
        185                 190                 195

GTG ACA ACA ACG GTC TCT ACC TTT GTT CCT CCA ATG CCT TTG CCC AGG            919
Val Thr Thr Thr Val Ser Thr Phe Val Pro Pro Met Pro Leu Pro Arg
    200                 205                 210

CAG AAC CAT GAA CCA GTA GCC ACT TCA CCA TCT TCA CCT CAG CCA GCA            967
Gln Asn His Glu Pro Val Ala Thr Ser Pro Ser Ser Pro Gln Pro Ala
215                 220                 225                 230

GAA ACC CAC CCT ACG ACA CTG CAG GGA GCA ATA AGG AGA GAA CCC ACC           1015
Glu Thr His Pro Thr Thr Leu Gln Gly Ala Ile Arg Arg Glu Pro Thr
                235                 240                 245

AGC TCA CCA TTG TAC TCT TAC ACA ACA GAT GGG AAT GAC ACC GTG ACA           1063
Ser Ser Pro Leu Tyr Ser Tyr Thr Thr Asp Gly Asn Asp Thr Val Thr
            250                 255                 260

GAG TCT TCA GAT GGC CTT TGG AAT AAC AAT CAA ACT CAA CTG TTC CTA           1111
Glu Ser Ser Asp Gly Leu Trp Asn Asn Asn Gln Thr Gln Leu Phe Leu
        265                 270                 275

GAA CAT AGT CTA CTG ACG GCC AAT ACC ACT AAA GGA ATC TAT GCT GGA           1159
Glu His Ser Leu Leu Thr Ala Asn Thr Thr Lys Gly Ile Tyr Ala Gly
    280                 285                 290

GTC TGT ATT TCT GTC TTG GTG CTT CTT GCT CTT TTG GGT GTC ATC ATT           1207
Val Cys Ile Ser Val Leu Val Leu Leu Ala Leu Leu Gly Val Ile Ile
295                 300                 305                 310

GCC AAA AAG TAT TTC TTC AAA AAG GAG GTT CAA CAA CTA AGA CCC CAT           1255
Ala Lys Lys Tyr Phe Phe Lys Lys Glu Val Gln Gln Leu Arg Pro His
                315                 320                 325

AAA TCC TGT ATA CAT CAA AGA GAA TAGTCCCTGG AAACATAGCA AATGAACTTC          1309
Lys Ser Cys Ile His Gln Arg Glu
            330
```

-continued

```
TATCTTGGCC ATCACAGCTG TCCAGAAGAG GGGAATCTGT CTTAAAAACC AGCAAATCCA    1369

ACGTGAGACT TCATTTGGAA GCATTGTATG ATTATCTCTT GTTTCTATGT TATACTTCCA    1429

AATGTTGCAT TTCCTATGTT TTCCAAAGGT TTCAAATCGT GGGTTTTTAT TTCCTCCGTG    1489

GGGAAACAAA GTGAGTCTAA CTCACAGGTT TAGCTGTTTT CTCATAACTC TGGAAATGTG    1549

ATGCATTAAG TACTGGATCT CTGAATTGGG GTAGCTGTTT TACCAGTTAA AGAGCCTACA    1609

ATAGTATGGA ACACATAGAC ACCAGGGGAA GAAAATCATT TGCCAGGTGA TTTAACATAT    1669

TTATGCAATT TTTTTTTTTT TTTTTGAGAT GGAGCTTTGC TCTTGTTGCC CAGGCTGGAG    1729

TGCGATGGTG AAATCTCGGC TCACTGTAAC CTCCACCTTC CGGGTTCAAG CAATTCTCCC    1789

GTCGAC                                                               1795
```

(2) INFORMATION FOR SEQ ID NO: 7:

(i) SEQUENCE CHARACTERISTICS:
        (A) LENGTH: 334 amino acids
        (B) TYPE: amino acid
        (D) TOPOLOGY: linear (ii) MOLECULE TYPE: protein (xi) SEQUENCE DESCRIPTION: SEQ ID NO: 7:

```
Met His Pro Gln Val Val Ile Leu Ser Leu Ile Leu His Leu Ala Asp
 1               5                  10                  15

Ser Val Ala Gly Ser Val Lys Val Gly Gly Glu Ala Gly Pro Ser Val
            20                  25                  30

Thr Leu Pro Cys His Tyr Ser Gly Ala Val Thr Ser Met Cys Trp Asn
        35                  40                  45

Arg Gly Ser Cys Ser Leu Phe Thr Cys Gln Asn Gly Ile Val Trp Thr
    50                  55                  60

Asn Gly Thr His Val Thr Tyr Arg Lys Asp Thr Arg Tyr Lys Leu Leu
65                  70                  75                  80

Gly Asp Leu Ser Arg Arg Asp Val Ser Leu Thr Ile Glu Asn Thr Ala
                85                  90                  95

Val Ser Asp Ser Gly Val Tyr Cys Cys Arg Val Glu His Arg Gly Trp
            100                 105                 110

Phe Asn Asp Met Lys Ile Thr Val Ser Leu Glu Ile Val Pro Pro Lys
        115                 120                 125

Val Thr Thr Thr Pro Ile Val Thr Thr Val Pro Thr Val Thr Thr Val
    130                 135                 140

Arg Thr Ser Thr Thr Val Pro Thr Thr Thr Val Pro Thr Thr Val Pro Thr Thr
145                 150                 155                 160

Val Pro Thr Thr Met Ser Ile Pro Thr Thr Thr Val Pro Thr Thr
                165                 170                 175

Met Thr Val Ser Thr Thr Thr Ser Val Pro Thr Thr Ser Ile Pro
            180                 185                 190

Thr Thr Thr Ser Val Pro Val Thr Thr Val Ser Thr Phe Val Pro
        195                 200                 205

Pro Met Pro Leu Pro Arg Gln Asn His Glu Pro Val Ala Thr Ser Pro
    210                 215                 220

Ser Ser Pro Gln Pro Ala Glu Thr His Pro Thr Thr Leu Gln Gly Ala
225                 230                 235                 240

Ile Arg Arg Glu Pro Thr Ser Ser Pro Leu Tyr Ser Tyr Thr Thr Asp
                245                 250                 255

Gly Asn Asp Thr Val Thr Glu Ser Ser Asp Gly Leu Trp Asn Asn Asn
```

-continued

```
                        260                     265                     270
    Gln Thr Gln Leu Phe Leu Glu His Ser Leu Leu Thr Ala Asn Thr Thr
            275                     280                     285

Lys Gly Ile Tyr Ala Gly Val Cys Ile Ser Val Leu Val Leu Leu Ala
            290                     295                     300

Leu Leu Gly Val Ile Ile Ala Lys Lys Tyr Phe Phe Lys Lys Glu Val
    305                     310                     315                     320

Gln Gln Leu Arg Pro His Lys Ser Cys Ile His Gln Arg Glu
                    325                     330
```

What is claimed is:

1. An isolated nucleic acid comprising a nucleotide sequence encoding a polypeptide comprising amino acids 1–290 of SEQ ID NO:7.

2. The isolated nucleic acid of claim 1, wherein the polypeptide comprises SEQ ID NO:7.

3. The isolated nucleic acid of claim 1, wherein the polypeptide further comprises an Ig Fc domain.

4. An isolated DNA comprising nucleotides 278–1147 of SEQ ID NO:6 or the DNA complement of nucleotides 278–1147 of SEQ ID NO:6.

5. The isolated nucleic acid of claim 4, wherein the nucleic acid comprises SEQ ID NO:6 or the complement of SEQ ID NO:6.

6. A vector comprising the nucleic acid of claim 1.
7. A vector comprising the nucleic acid of claim 2.
8. A vector comprising the nucleic acid of claim 3.
9. A vector comprising the nucleic acid of claim 4.
10. A vector comprising the nucleic acid of claim 5.
11. A host cell comprising the nucleic acid of claim 1.
12. A host cell comprising the nucleic acid of claim 2.
13. A host cell comprising the nucleic acid of claim 3.
14. A host cell comprising the nucleic acid of claim 4.
15. A host cell comprising the nucleic acid of claim 5.

16. An isolated DNA comprising a nucleotide sequence encoding a polypeptide comprising amino acids 21–290 of SEQ ID NO:7.

17. A nucleic acid comprising a nucleotide sequence encoding a polypeptide comprising a mammalian KIM1 polypeptide lacking a KIM1 signal sequence, the mammalian KIM1 polypeptide being selected from the group consisting of SEQ ID NO:3 and SEQ ID NO:7.

18. The nucleic acid of claim 17, wherein the encoded polypeptide further lacks a transmembrane domain.

19. A nucleic acid comprising a nucleotide sequence encoding a fusion protein comprising amino acids 21–290 of SEQ ID NO:7 and an Fc region of an immunolobulin.

* * * * *